(12) United States Patent
Lynch et al.

(10) Patent No.: US 6,511,817 B1
(45) Date of Patent: Jan. 28, 2003

(54) METHODS AND DEVICE FOR IN VITRO DETECTION AND CHARACTERIZATION OF PSYCHOACTIVES USING ANALYSIS OF REPETITIVE ELECTRICAL ACTIVITY IN A NEURONAL SAMPLE

(75) Inventors: Gary Lynch, Irvine, CA (US); Makoto Taketani, Irvine, CA (US); Ken Shimono, Irvine, CA (US); Hirokazu Sugihara, Katano (JP)

(73) Assignees: Matsushita Electric Industrial Co., Ltd., Osaka (JP); University of California, Oakland, CA (US)

( * ) Notice: Subject to any disclaimer, the term of this patent is extended or adjusted under 35 U.S.C. 154(b) by 13 days.

(21) Appl. No.: 09/602,629

(22) Filed: Jun. 21, 2000

Related U.S. Application Data

(60) Provisional application No. 60/140,339, filed on Jun. 21, 1999.

(51) Int. Cl.[7] .............. C12Q 1/02; C12Q 1/00; C12M 1/34; C12M 1/00; C25D 17/00
(52) U.S. Cl. ............ 435/29; 435/4; 435/283.1; 435/287.1; 435/285.2; 702/19; 204/222
(58) Field of Search ............ 435/29, 4, 283.1, 435/285.2, 287.1; 702/19; 204/222

(56) References Cited

U.S. PATENT DOCUMENTS

| | | | | |
|---|---|---|---|---|
| 4,385,053 A | * | 5/1983 | Reisberg et al. | 424/199 |
| 5,759,846 A | | 6/1998 | Stoppini et al. | 435/29 |
| 5,772,983 A | | 6/1998 | O'Connell et al. | 435/29 |
| 5,902,732 A | | 5/1999 | Hochman | 435/29 |

FOREIGN PATENT DOCUMENTS

| | | |
|---|---|---|
| EP | 0 689 051 A3 | 12/1995 |
| EP | 0 689 051 A2 | 12/1995 |
| WO | WO 93/15184 A1 | 8/1993 |
| WO | WO 99/20315 A1 | 4/1999 |
| WO | 200079273 A2 * | 12/2000 |
| WO | 200156647 * | 8/2001 |

OTHER PUBLICATIONS

Chay, T. R. (1996). "Eletrical Bursting and Luminal Calcium Oscillation in Excitable Cell Models," *Biological Cybernetics* 75(5):419–431.

Malouf, A. T. et al. (1988). "Comparison of the Actions of the Phencyclidine and Sigma Ligands on Cai Hippocampal Pyramidal Neurons in the Rat," *Neuropharmacology* 27(11):1161–1170.

Monnet, F. P. et al. (1992). "In Vivo Electrophysiological Evidence for a Selective Modulation of N–Methyl–D–Aspartate–Induced Neuronal Activation in Rat CA3 Dorsal Hippocampus by Sigma Ligands," *Journal of Pharmacology and Experimental Therapeutics* 21(1):123–130.

* cited by examiner

*Primary Examiner*—Louise N. Leary
(74) *Attorney, Agent, or Firm*—Morrison & Foerster LLP

(57) ABSTRACT

This relates to methods for the detection of psychoactive compounds in an in vitro neuronal tissue sample by detecting oscillations of extracellular voltage desirably before and after the introduction of a candidate sample onto an in vitro neuronal tissue sample and for devices useful in practicing the methods. Analysis of the extracellular voltage parameters leads to indication of the presence of psychoactive material in the candidate sample and information as to its pharmacological activity and/or composition. Further, it relates to a process of initiating and maintaining the presence of repetitive neuronal activity within the in vitro sample. Additionally, this includes a method for the stimulation of or initiation of repetitive neuronal activity, e.g., EEG, in an in vitro neuronal tissue sample by introducing a stimulating composition comprising compounds that facilitate or mimic the actions of acetylcholine, serotonin, or catecholamines, such as carbachol, or by subjecting the in vitro neuronal sample to electrical stimulation parameters.

52 Claims, 36 Drawing Sheets

Original     Sampled (aliased)     Sampled & anti-aliased

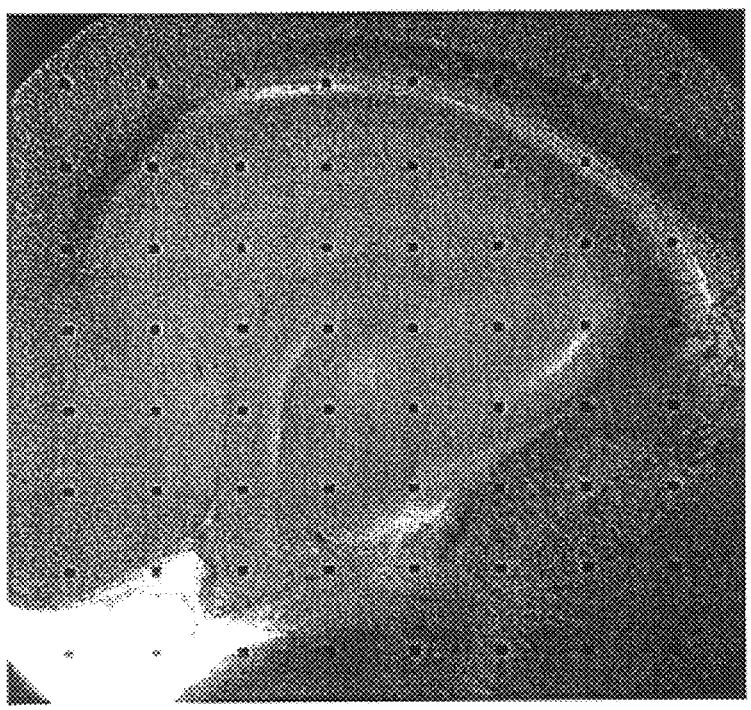
Fig. 6A
Fig. 6B
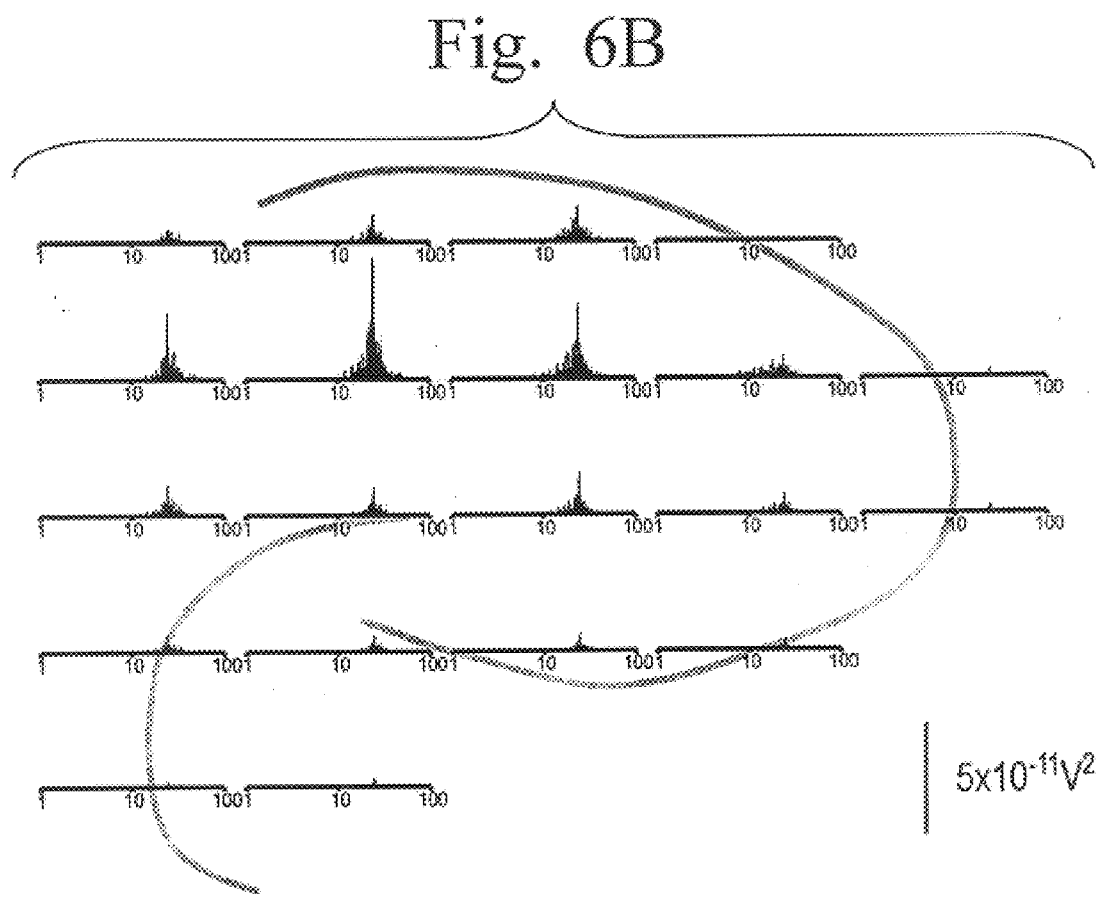
$5 \times 10^{-11} V^2$

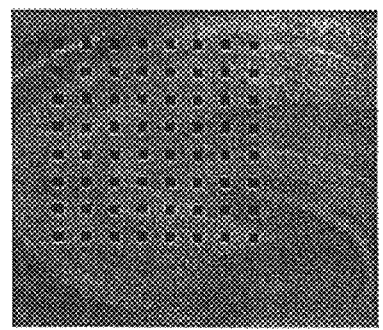
Fig. 7A
Fig. 7B
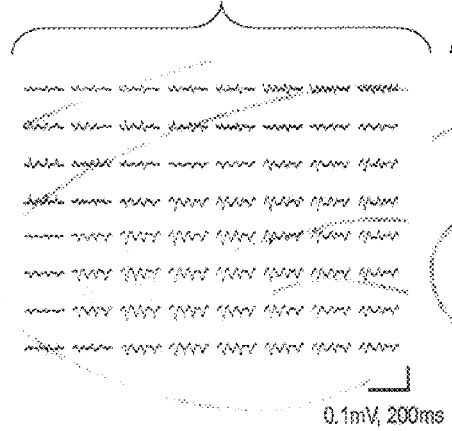
0.1mV, 200ms
Fig. 7C
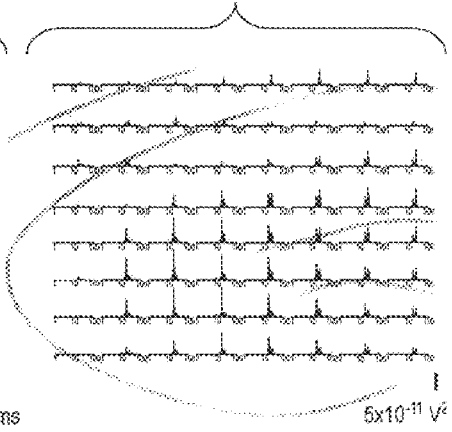
5x10⁻¹¹ V²

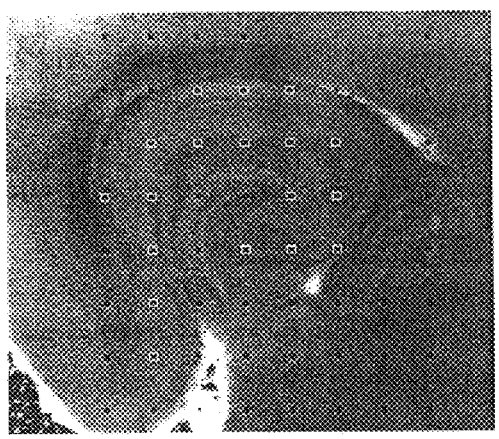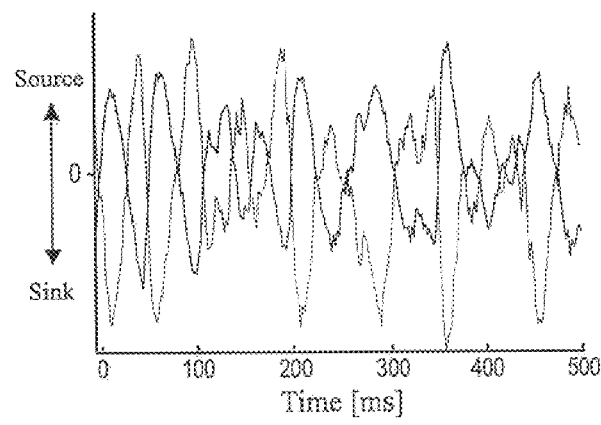
Fig. 9A
Fig. 9B

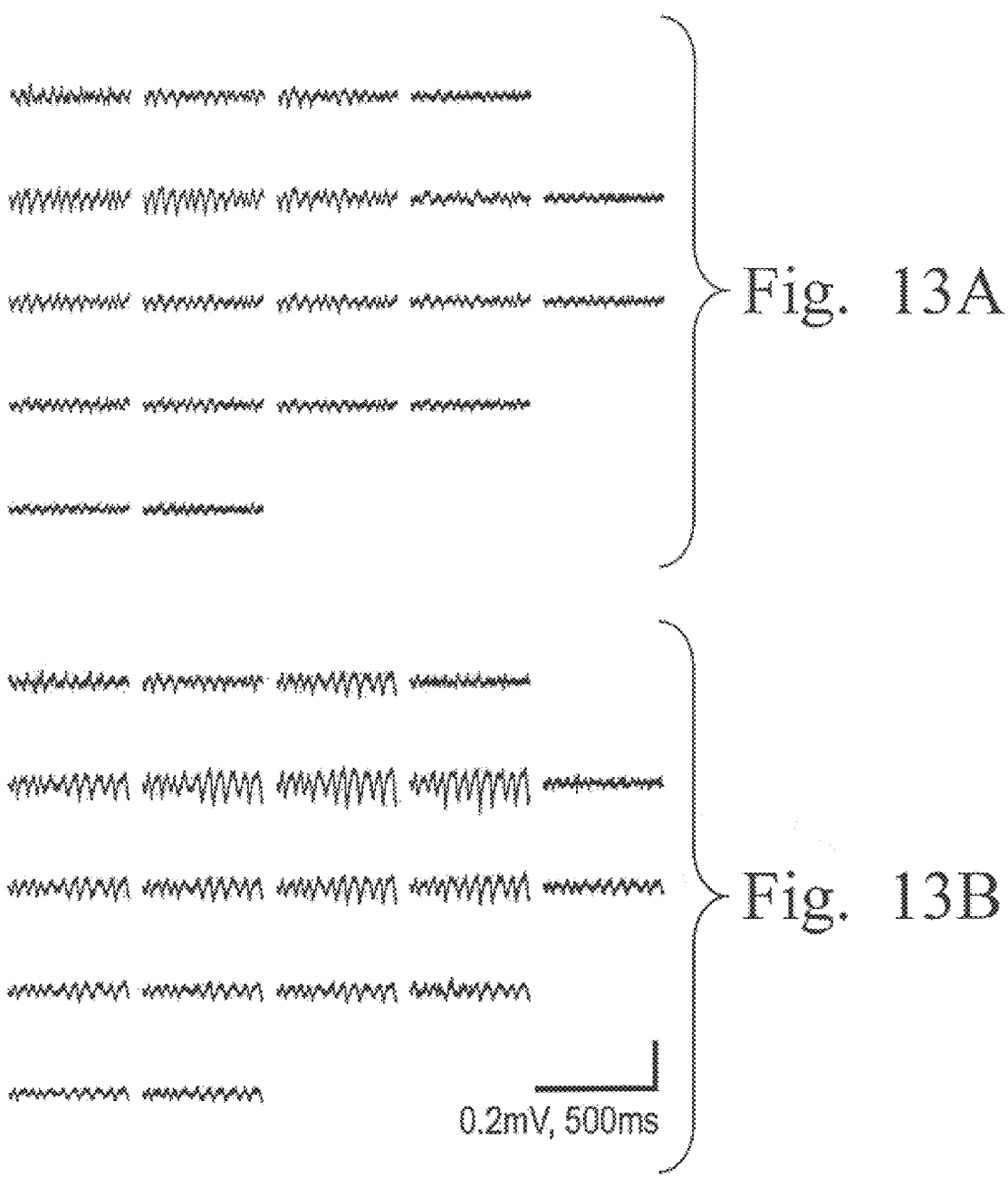

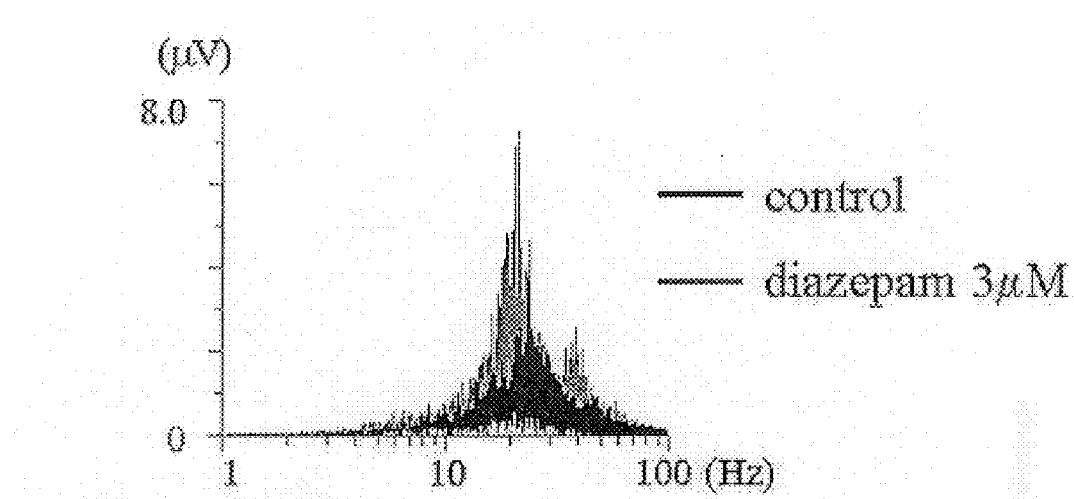
Fig. 15C
Fig. 15B
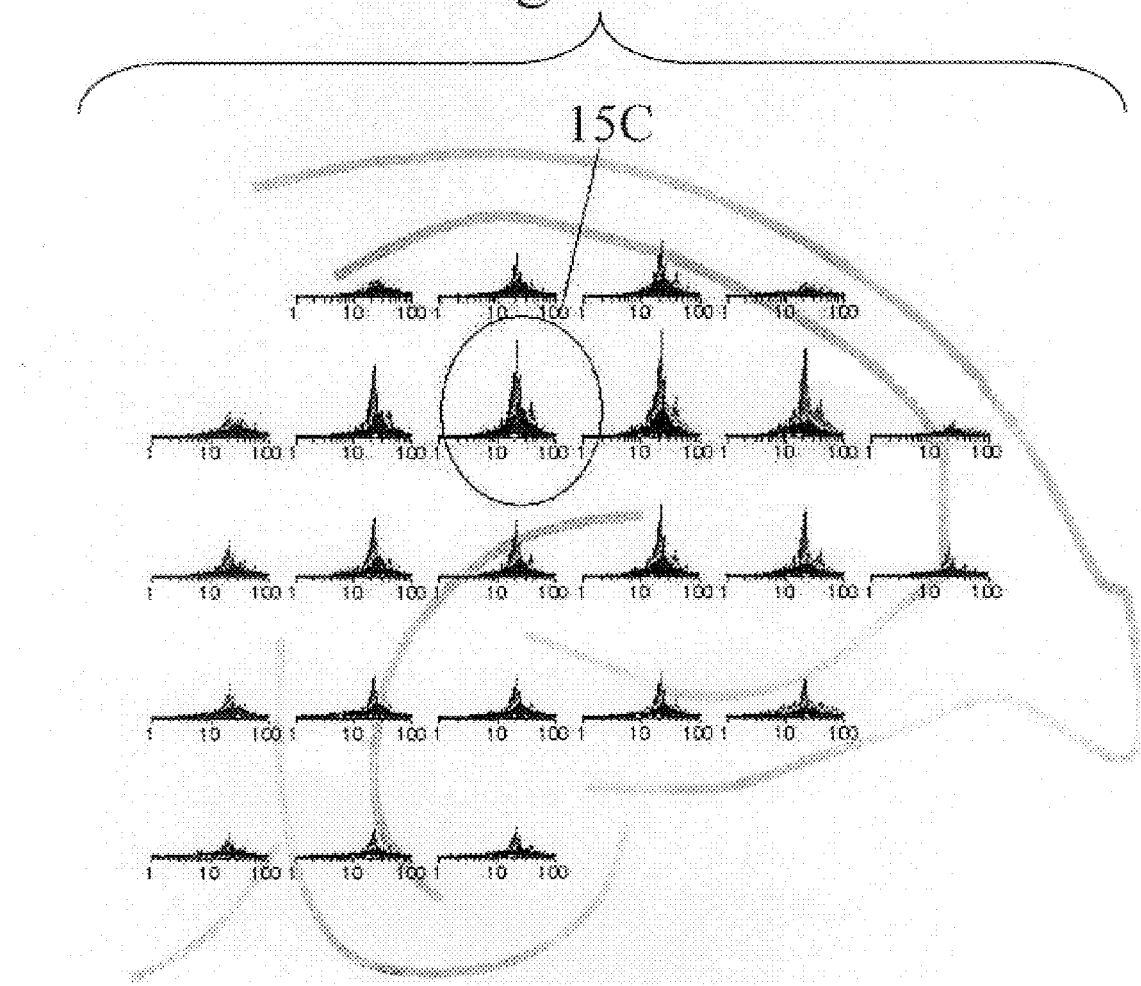

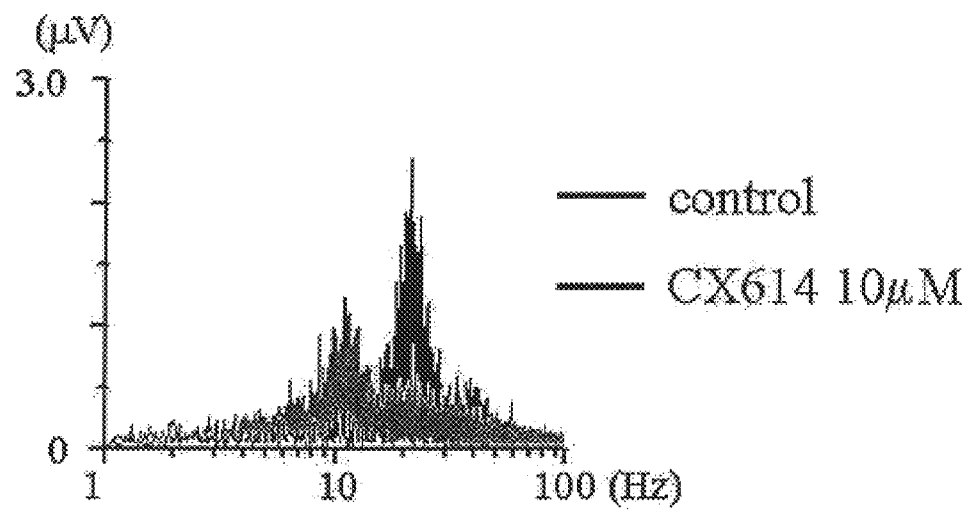
Fig. 16C
Fig. 16B
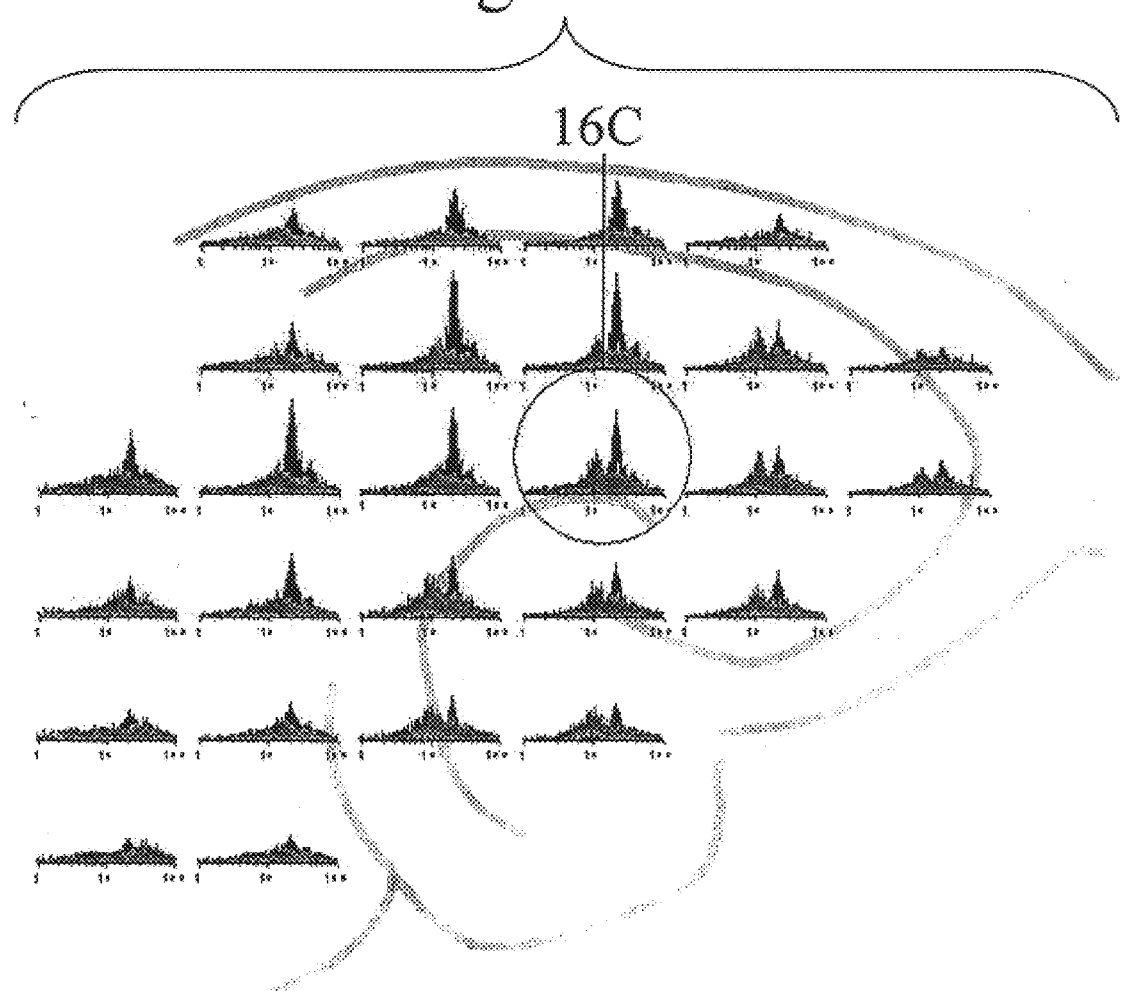

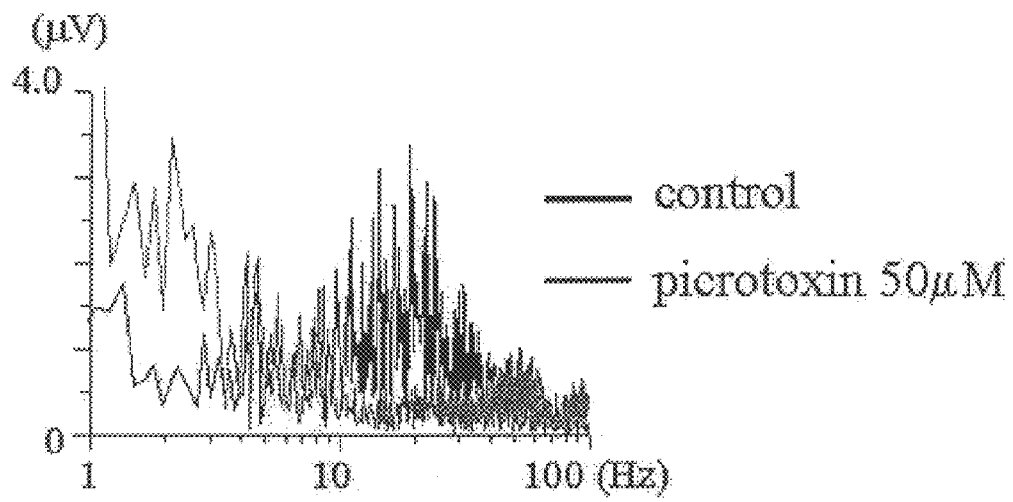
Fig. 19C
Fig. 19B
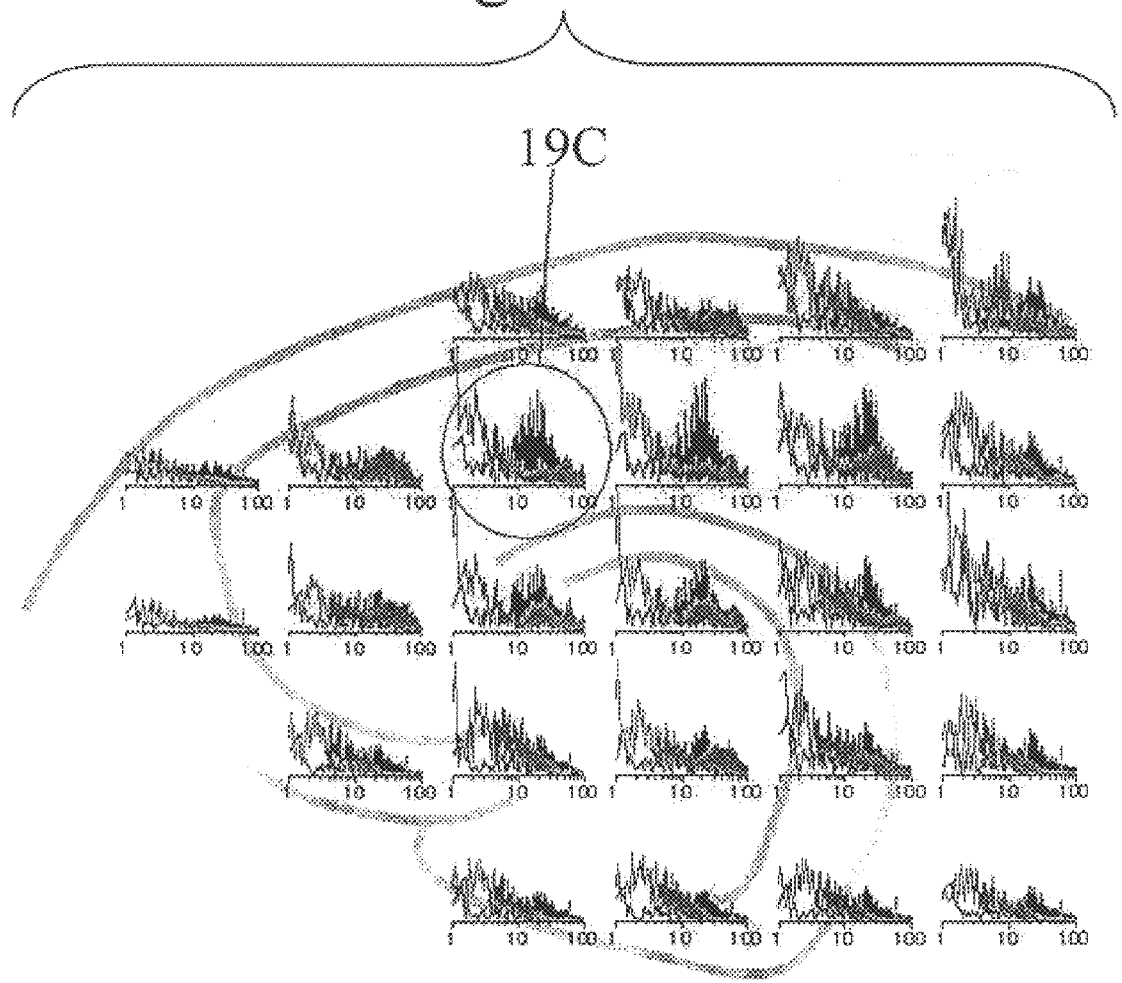

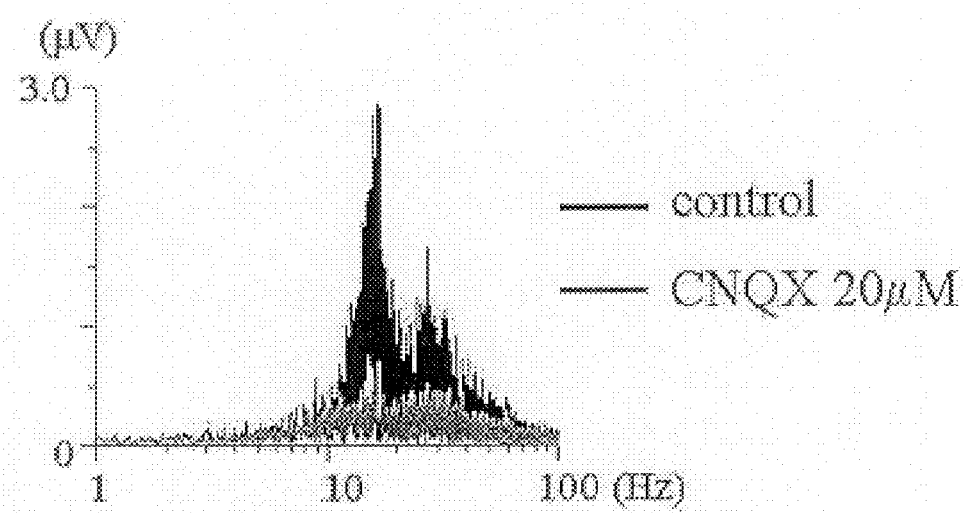
Fig. 20C
Fig. 20B
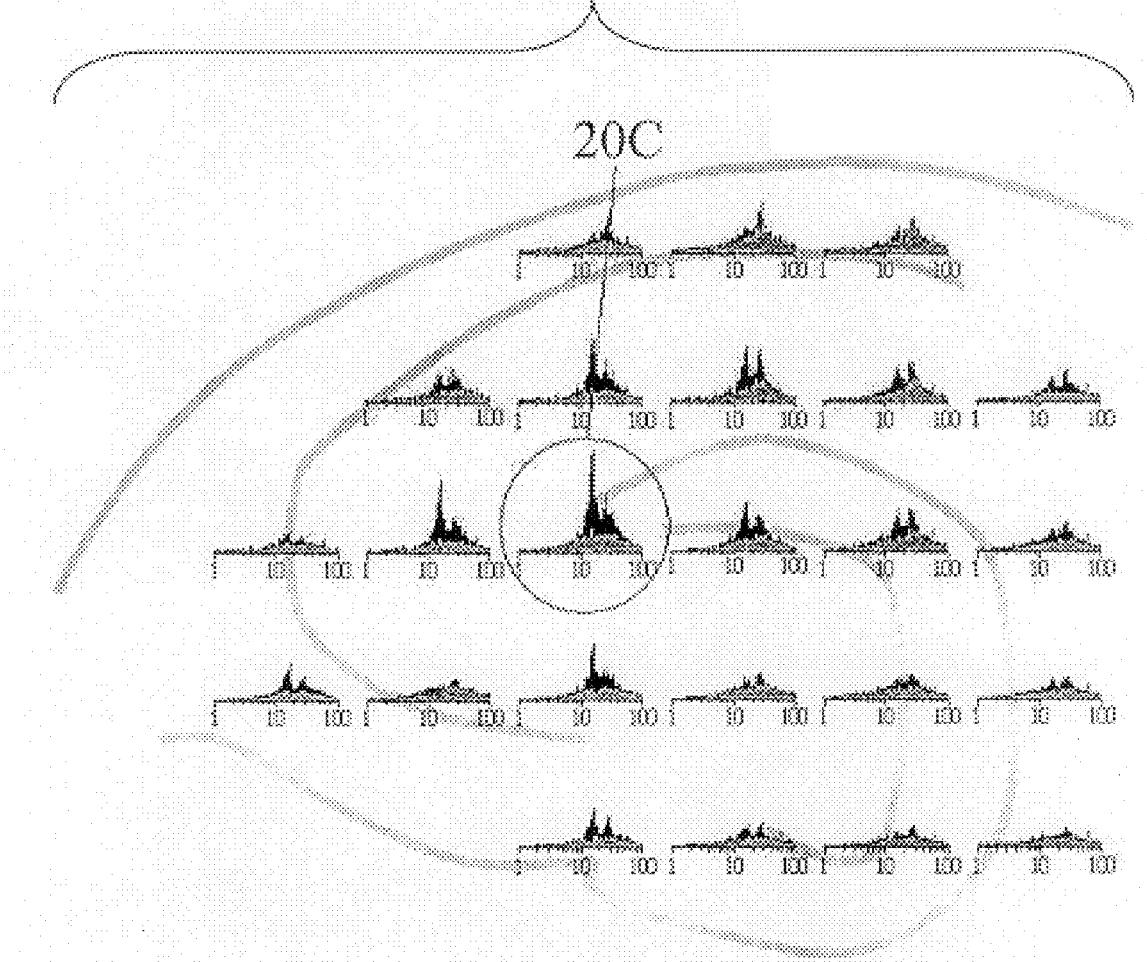

METHODS AND DEVICE FOR IN VITRO DETECTION AND CHARACTERIZATION OF PSYCHOACTIVES USING ANALYSIS OF REPETITIVE ELECTRICAL ACTIVITY IN A NEURONAL SAMPLE

This application claims the benefit of Provisional Application No. 60/140,339, filed Jun. 21, 1999.

FIELD OF THE INVENTION

This invention relates to methods for the detection of psychoactive compounds in an in vitro neuronal tissue sample, preferably by detecting oscillations of extracellular voltage of before and after the introduction of a candidate sample onto an in vitro neuronal tissue sample and to devices for practicing those processes. Analysis of the extracellular voltage parameters leads to indication of the presence of psychoactive material in the candidate sample and information as to its pharmacological activity and composition. Further, the invention includes a process of initiating and maintaining the presence of repetitive neuronal activity within the in vitro sample. Additionally, this invention includes a method for the stimulation of or initiation of repetitive neuronal activity, e.g., EEG, in an in vitro neuronal tissue sample by introducing a stimulating composition comprising compounds that facilitate or mimic the actions of acetylcholine, serotonin, or catecholamines, such as carbachol.

BACKGROUND OF THE INVENTION

Rhythmic activity in the hippocampus of small mammals is described as falling into three frequency bands: 4–10 Hz (theta), 10–30 Hz (beta), and above 30 Hz (gamma) (Traub et al., 1998; 1999 for a recent discussion). Theta is by far the best studied of these and is related to, among other things, locomotor activity (Vanderwolf, 1969) and memory encoding (Landfield et al., 1972; Vertes and Kocsis, 1997). In accord with the latter idea is the close relationship between theta and long-term potentiation (Larson and Lynch, 1986; Larson et al., 1986, 1993), a probable substrate of certain forms of memory. The functional correlates of the higher frequency rhythms have recently become the subjects of considerable interest. Gamma activity was first analyzed in the olfactory system (Freeman, 1975 for an early review) with the conclusion that it allows coherence to develop between bulb, piriform cortex, and entorhinal cortex prior to the arrival of an odor (Kay and Freeman, 1998). Activity falling in the gamma range also appears in the visual cortex during cue presentation (Gray and Singer, 1989) where it is proposed to transiently synchronize cells with disparate receptive fields. Synchronization, according to this hypothesis, allows multiple features of a cue to be assembled into a coherent representation (Singer, 1998 for a review). Beta rhythms have not typically been discriminated from the gamma wave in discussions of high frequency hippocampal activity although they have been selectively induced in hippocampal slices (Boddeke et al, 1997). In any event, the growing evidence that high frequency synchronization in essential to coherent operations in the cortical telencephalon has emphasized the importance of identifying the pathways and neurotransmitter systems responsible for the beta and gamma oscillations.

Ascending cholinergic projections promote endogenous oscillations including those in the beta and gamma ranges. Although early work (Stumpf, 1965) found cholinergic blockers or septal lesions to be without obvious effect, subsequent studies showed that fast waves in freely moving rats are enhanced by the cholinesterase inhibitor physostigmine and substantially reduced by antagonists (Leung, 1985). Cholinergic stimulation of hippocampal or entorhinal slices is usually described as inducing seconds-long episodes of theta-like activity (Konopacki et al., 1987; MacVicar and Tse, 1989; Dickson and Alonso, 1997; Williams and Kauer, 1997) but recent experiments show that it can also trigger higher frequency rhythms (20–40 Hz) in cortical and hippocampal slices (Boddeke et al., 1997; Fisahn et al., 1998). Cholinergic. septohippocampal fibers innervate discrete regions of the hippocampal system (Lewis and Shute, 1967; Mosko et al., 1973; Frotscher and Leranth, 1985; Matthews et al., 1987) where they contact subpopulations of interneurons and select dendritic zones of principal cells (Mosko et al., 1973; Lynch et al., 1978; Matthews et al., 1987). Stimulation of muscarinic receptors depolarizes pyramidal cells, depresses release from some interneurons, and increases the excitability of others (Pitler and Alger, 1992; Behrends and Bruggencate, 1993). The combination of in vivo and in vitro results suggests that acetylcholine plays an important role in generating high frequency activity in the cortical telencephalon.

How cholinergically driven high frequency rhythms affect cortical operations depends on whether they are regionally specialized and how they are produced. Carbachol-elicited oscillations are reported to originate in restricted loci in entorhinal cortex (Dickson and Alonso, 1997) and hippocampus (Fisahn et al., 1998) but a more general answer requires systematic mapping over broad expanses of the entorhinohippocampal system. This invention made use of a recently introduced device (Oka et al, 1999) for simultaneously recording from 64 sites to address the origins and regional variations in cholinergically induced high frequency rhythms in the hippocampal cortex.

In addition to the location of the sources, we have found that the oscillations themselves may be studied using various mathematical tools both to identify the presence of psychoactive materials and, in some instances at least, identify and characterize the pharmacological activity or composition of the psychoactive material.

None of the documents discussed above utilize the high frequency oscillations found in the in vitro samples for indication of the presence of, characterization of the pharmacological activity of, or the composition of the psychoactive material.

SUMMARY OF THE INVENTION

The inventive methods here include a method for detection of, characterization of the pharmacological activity, and for determining the composition of psychoactive compounds in an in vitro neuronal tissue sample. An allied inventive method is a method for the stimulation of the initiation and stimulation of repetitive neuronal activity variously by the steps of adding a composition that stimulates those oscillations of extracellular voltage, or utilizes a co-implanted bit of neuronal tissue, or stimulates the neuronal sample using an electrical stimulation pattern.

In general, the preferred method for detection of psychoactive compounds in an in vitro neuronal tissue sample includes the steps of inducing and then detecting the presence of oscillations in the tissue sample and providing a baseline value of those oscillations. After that detection, the in vitro sample is brought into contact with a candidate sample of a psychoactive compound or compounds. Coincidentally with (or subsequent to) introduction of the candidate sample, the oscillations, e.g., EEG waves, are then measured. The two sets of oscillation data are then rendered to produce respectively two so-called "calculated values." Comparing the two calculated values will then allow detection, characterization of the pharmacological activity, and determination of the composition of psychoactive compounds in the sample should one or more be present.

The various oscillations are typically those found in extracellular voltage. For instance, they may be a theta, beta, or gamma EEG waves.

It is desirable to use a multi-electrode dish ("MED") so that a number of different active or less active sites on the neuronal sample may be simultaneously or sequentially sampled. Use of the MED permits measurement and calculation of spatial relationships; both measured and calculated, amongst the values of the neural oscillations. The multi-electrode nature of the MED also enables the determination and characterization of region-specific effects within the given in vitro neuronal sample.

Appropriate mathematical analysis of the oscillations of extracellular voltage include a Fast Fourier Transform (FFT) of oscillations measured at a single spatial point to enhance differences in amplitude and frequency of the before-and-after single-site measurements.

Similarly, the sequence of oscillations of extra-cellular voltage obtained in an array as a function of time may be subjected to Current Source Density (CSD) analysis to produce and depict current flow patterns within the in vitro neuronal tissue sample.

A further portion of the invention includes the use of chemical or anatomical compositions and electrical stimulation patterns that tend to stimulate or induce repetitive neuronal activity in in vitro neuronal tissue samples. These compositions may be compounds that mimic or facilitate the actions of acetylcholine, serotonin, or catecholamines. They may be co-deposited neuronal tissue. They may be cholinomimetic compounds. A highly desirable chemical compound is carbachol. Electrical stimulations may also be used.

The invention includes various methods of detection, characterization of the pharmacological activity, and determination psychoactive test compound composition. A number of methods for identifying those test compounds are within the methods of the invention.

BRIEF DESCRIPTION OF THE DRAWINGS

The accompanying drawings illustrate and explain the principles of the invention. They are not intended to limit the scope of the invention in any way.

FIGS. 6A to 6E show a micrograph of a hippocampal slice and the distribution of carbachol-induced beta waves within the hippocampus.

FIGS. 7A–7C show carbachol-induced beta waves in a hippocampus measured with a dense microelectrode array.

FIGS. 9A and 9B show the relationship of recurring carbachol-induced oscillations in apical and basal dendrites.

FIGS. 15A–C show the effect of flurazeparn on carbachol-induced beta waves.

FIGS. 16A–C show the effect of ampakine (CX614) on carbachol-induced beta waves.

FIGS. 19A–C show the effect of picrotoxin on carbachol-induced beta waves.

FIGS. 20A–C show the effect of CNQX on carbachol-induced beta waves.

DETAILED DESCRIPTION OF THE INVENTION

Figure 1:
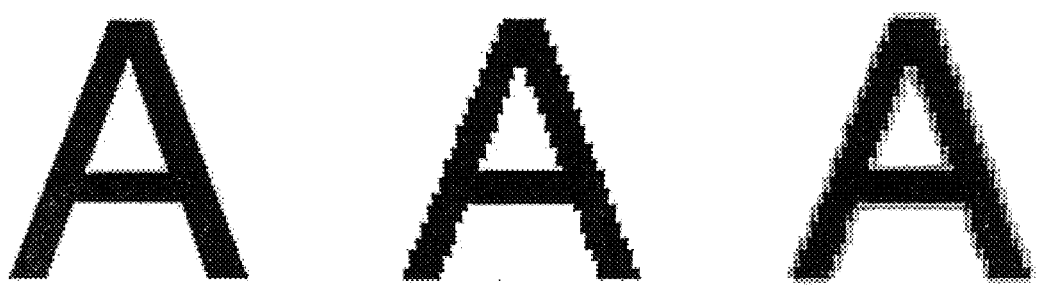
FIG. 1 depicts the phenomenon of "aliasing" in depicting measured images at low resolution.

This invention includes a process for the detection or characterization of psychoactive compositions preferably using rhythmic oscillations of extracellular voltage (or potential) in in vitro neuronal tissue samples. Additionally, the inventive process comprises the stimulation or inducement of those oscillations using certain classes of compositions or electrical stimulation techniques that are discussed in more detail below.

The measurement of extracellular potentials in in vitro neuronal tissue over the spatial array of a neuronal sample is known. See, for instance, the various descriptions of such devices found in U.S. Pat. Nos. 5,563,067 and 5,810,725, each to Sugihara et al.

Measuring Apparatus

The cell potential measuring electrode array preferably used with this inventive process includes plural microelectrodes on an insulating substrate, a conductive pattern for connecting the microelectrodes to some region out of the microelectrode area, electric contacts connected to the end of the conductive pattern, an insulating film covering the surface of the conductive pattern, and a wall enclosing the region including the microelectrodes on the surface of the insulating film. The reference electrodes may have comparatively lower impedance than the impedance of the measuring microelectrodes. They may be placed at plural positions in the region enclosed by the wall and often at a specific distance from the microelectrodes. The electrical contacts are further usually connected between the conductive pattern for wiring of each reference electrode and the end of the conductive pattern. The surface of the conductive pattern for wiring of the reference electrodes is typically covered with an insulating film.

Typically, the microelectrodes are situated in a matrix arrangement in a rectangle having sides of, e.g., 0.8 to 2.2 mm (in the case of 300 μm microelectrode pitch) or 0.8 to 3.3 mm (in the case of 450 μm microelectrode pitch). Four reference electrodes are situated at four corners of a rectangle of 5 to 15 mm on one side. More preferably, 64 microelectrodes are situated in eight rows and eight columns at central pitches of about 100 to 450 μm, preferably 100 to 300 μm.

Preferably the microelectrodes and the reference electrodes are formed of layers of nickel plating, gold plating, and platinum black on an indium-tin oxide (ITO) film.

The insulating substrate (for example, a glass substrate) may be nearly square. Plural electric contacts may be connected to the end of the conductive pattern and preferably are placed on the four sides of the insulating substrate. As a result, layout of wiring patterns of multiple microelectrodes and reference electrodes is easy. Because the pitches of electric contacts may be made to be relatively large, electric connection through the electric contacts with external units is also easy.

The microelectrode region is usually very small. When observing the sample through a microscope, it is hard to distinguish position and both vertical and lateral directions. It is desirable to place indexing micro-marks near the microelectrode region to allow visual recognition through the microscope variously of direction, axes, and position.

It is even more preferable to perform the following sequence of events to determine electrode positions versus the anatomical correlates of the in vitro neuronal samples. Placing a control in vitro neuronal sample on the array in order that the array can cover the important area of the sample, taking a picture of the control sample on the array, recording the response from the control sample, placing a test sample on the array in the same relative position as the control sample as accurately as possible, taking a picture of the test sample on the array, recording the response from the test sample, and comparing the control picture and the test picture, and comparing the control response and the test response.

An alternative method, which would be appreciated by one skilled in the art, is to use an object recognition algorithm where the object is the gross anatomical structure of the in vitro neuronal samples, and comparing object recognition algorithm data, and comparing the control response and the test response.

The most preferred cell potential measuring apparatus is made up of a cell placement device having cell potential measuring electrodes, contact sites for contacting with an electric contact, and an electrode holder for fixing the insulating substrate by sandwiching from above and beneath. The cell potential measuring electrodes may be connected electrically to the cell placement assembly device to allow processing of the voltage or potential signals generated by the sample and measured between each such microelectrode and the reference electrodes. The cell potential measuring assembly may include a region enclosed by a wall for cultivating sample neuronal cells or tissues. It also preferably includes an optical device for magnifying and observing optically the cells or tissues cultivated in the region enclosed by the wall. This cell potential measuring apparatus preferably further comprises an image memory device for storing the magnified image obtained by the optical device.

Typically a personal computer having installed measurement software is included to accept the measured cell potentials. The computer and cell placement device are typically connected through an I/O board for measurement. The I/O board includes an A/D converter and a D/A converter. The A/D converter is usually for measuring and converting the resulting potentials; the D/A converter is for stimulus signals to the sample, when needed.

The measurement software installed in the computer may include software for setting conditions for giving a stimulus signal, forming the stimulus signal, and for recording the obtained detection signal. By using such measurement software, the computer may comprise means for giving a stimulus signal to the cells and means for processing the signal detected from the cells. The computer may also control any optical observation devices (SIT camera and image memory device) and the cell culture system.

Desirably, the extracellular potential detected from the cells may be displayed in real time. In addition, the recorded spontaneous activity, potential, or induced potential desirably is displayed by overlaying on the microscope image of the cell. It is an alternative that the software also include image processing, e.g., feature recognition, edge detection, or edge enhancement, algorithmic capabilities. When measuring the potential, the entire recorded waveform is usually displayed visually correlated to the position of the waveform in the neuronal sample.

Concerning data analysis or processing, Fast Fourier Transform (FFT) analysis, coherence analysis, and correlation analysis are also desirable. In the variation discussed below, Current-Source Density Analysis (CSD) is also highly desirable. Other useable functions may include single spike separation function using waveform discrimination, temporal profile display function, and topography display function. These analysis results may be displayed by overlaying on the displayed images of the neuronal sample stored in the image memory device.

When a stimulus signal is issued from the computer, this stimulus signal is sent to the cell placement device through a D/A converter and an isolator. The cell placement device includes a cell potential measuring electrode that may be formed, e.g., of 64 microelectrodes on a glass substrate in a matrix form and having an enclosing wall for maintaining the neuronal sample (e.g., segments of cells or tissues) in contact with the microelectrodes and their culture fluid. Preferably, the stimulus signal sent to the cell placement device is applied to arbitrary electrodes out of the 64 microelectrodes and then to the sample or samples.

The induced, evoked, or spontaneous potential occurring between each microelectrode and reference potential (which is at the potential of the culture fluid) is passed through a 64-channel high sensitivity amplifier and an A/ID converter into the computer. The amplification factor of the amplifier may be, e.g., about 80–100 dB, for example, in a frequency band of about 0.1 to 10 kHz, or to 20 Hz. However, when measuring the potential induced by a stimulus signal, by using a lowcut filter, the frequency band is preferably 100Hz to 40kHz or more.

The desired apparatus may include a cell culture system having a temperature controller, a culture fluid circulation device, and a feeder for supplying, e.g., a mixed gas of air and carbon dioxide. The cell culture system may be made up of a commercial microincubator, a temperature controller, and $CO^2$ cylinder. The microincubator can be used to control in a temperature range of 0 to 50° C. by means of a Peltier element and is applicable to the liquid feed rate of 3.0 ml/min or less and gas flow rate of 1.0 liter/min or less. Or, alternatively, a microincubator incorporating a temperature controller may be used.

Data Measurement and Analysis

In general, the procedures described herein utilize simultaneous measurement and preferably recording of extracellular voltage or potential values both spatially and temporally at each of such measurement sites. It is further preferable to observe the frequency and amplitude of the signals at each of the measurement sites in the spatial array. It is even more preferable that the placement of neuronal sample and the inherent physical boundaries in the sample be observable either using optical devices or electronic sensing devices and that those margins be correlated to the position of the sensors, all within the chosen computer.

The neuronal sample is placed upon said in vitro cell potential measuring electrode array and procedures that would be known to one skilled in the art are used for maintaining its viability during the testing. The neuronal sample may be cultured, if desired. Typical procedures are discussed below with respect to the Examples. Each of the microelectrodes is monitored, both as a function of time and as a function of frequency, for rhythmic oscillations of extracellular voltages or potentials. This produces an array of frequency and amplitude signals as a function of time. It is preferable to measure the oscillations from a region of near DC at 2 Hz to a region above 35 Hz. This permits measurement retention of the typical three frequency bands found in neuronal rhythmic activity: 4 to 20 Hz (theta EEG), 15 to 25 Hz (beta EEG), and above 30 Hz (gamma EEG). The higher frequency band of 10 to 50 Hz, is significantly instructive.

We have found it desirable to induce or stimulate oscillations of extracellular voltage or potential variously by pharmacological, physiological, or anatomical methods. It is preferable to use pharmacological compositions, e.g., one or more compounds that facilitate or mimic the actions of acetylcholine, serotonin, or catecholamines in this neuronal tissue, however, other stimulations are acceptable. It is even more preferable that said chemical stimulating compositions are one or more cholinominetic compounds of which carbachol (carbyl choline chloride) is highly desirable.

Once the noted materials have been added to the in vitro neuronal tissue sample, a set of baseline values of the oscillations is then taken.

A candidate sample composition that may or may not contain a psychoactive compound is then contacted with the in vitro neuronal tissue sample. An array of extracellular voltages or potentials is then measured. We have found that a comparison of these oscillatory extracellular voltages before and after the introduction of psychoactive compound (s) provides information on the presence of and/or characterization of psychoactive compositions. More details on specific compounds will be provided below in the Examples.

One procedure providing significant information as to the presence of or characterization of psychoactive compounds is the use of Fast Fourier Transforms (FFT). FFT are used in a variety of disparate areas and are commonly used in a device known as a spectrum analyzer. The application of FFT to specific measurement in the measurement array and comparing that result to a specific measurement at that same location prior to the introduction of the candidate composition will be instructive as to the presence, characterization, or pharmacological activity of a psychoactive compound. Specifically, if the candidate is psychoactive in the region of the neuronal sample that is analyzed, a comparison of the so-analyzed signals may show a shift in peak frequencies, amplitudes, or a combination of the two.

Another analysis, which is also instructive, is Current Source Density (CSD) analysis. A discussion of this analytical procedure is found, e.g., in Nicholson et al., "Theory of Current Source Density Analysis and Determination of Conductivity Tensor for Anuran Cerebellum," Journal of Neurophysiology, 1975, March, 38(2):356–68. This analytical procedure is used to convert the potentials or voltages measured by the devices described above, and convert them into a similar configured array of current flows and, more importantly, current magnitudes. By correlating the magnitude and direction of the currents as a function of time, current "sinks" and "sources" may be observed. The locations of such "sinks" and "sources" are instructive in determining the presence, characterization, or pharmacological activity of psychoactive drugs added to the in vitro neuronal sample.

As used herein, the term "sink" refers to current being absorbed from the extracellular medium into a neuronal element.

As used herein, the term "source" refers to current being injected into the extracellular medium from within a neuronal element.

As used herein, the term "hippocampus" refers to a region of the telencephalon which is located behind the temporal lobes and has been implicated in memory formation and retrieval in humans and other animals.

As used herein, the term "hippocampal slice" refers to a physical slice of hippocampal tissue generally approximately 100–500 micrometers in thickness that can be used on the electrophysiological recording apparatus described herein.

As used herein, the term "CA1", "Ce", "CA3", and "CA4" refer to one of four regions of hippocampus.

As used herein, the term "dendrites" refers to the highly branched structure emanating from the cell body of the nerve cells.

EXAMPLES

The Examples made use of a multi-electrode dish (MED) for simultaneously recording from 64 sites to address the origins and regional variations in cholinergically induced high frequency rhythms in a hippocampal cortex. Additional pharmacological and physiological studies relating to the oscillations were then conducted.

Preparation of Multi-electrode Array (the MED probe)

The general procedures for the preparation of the Multi-Electrode Dish (Matsushita Electric Industrial Co. Ltd., Osaka, Japan: "the MED probe") were described above. Procedures for the MED probe preparation are also described by Oka et al. (999). The device has an array of 64 planar microelectrodes, each having a size of 50×50 $\mu$m, arranged in an 8 by 8 pattern. Probes come with two types of interpolar distance, 150 $\mu$m (Panasonic: MED-P515AP) and 450 $\mu$m (Panasonic: MED-P545AP).

To provide sufficient adhesion of the neuronal sample slice to the MED surface, the surface of the MED probe was treated with 0.1% polyethylenimine (Sigma: P-3143) in 25 mM borate buffer, pH 8.4, for 8 hours at room temperature. The probe surface was rinsed 3 times with sterile distilled water. The probe (chamber) was then filled with DMEM/F-12 mixed medium, containing 10% fetal bovine serum (GIBCO: 16141-079) and 10% horse serum (GIBCO: 16050-122), for at least 1 hour at 37° C. DMEM/F-12 mixed medium is a 1:1 mixture of Dulbecco's Modified Eagle's Medium and Ham's F-12 (GIBCO: D/F-12 medium, 12400-024), supplemented with N2 supplement (GIBCO: 17502-014) and hydrocortisone (20 nM, Sigma, H0888).

Preparation of Hippocampal Slices

A 17–24 day old Sprague-Dawley rat was sacrificed by decapitation after anesthesia using halothane (2-Bromo-2 chloro-1,1,1 -trifluoroethane, Sigma: B4388), and the whole brain was removed carefully. The brain was immediately soaked in ice-cold, oxygenated preparation buffer of the following composition (in mM): 124 NaCl, 26 NaHCO$_3$, 10 glucose, 3 KCl, 1.25 NaH$_2$PO$_4$, 2 CaCl$_2$, 2 MgSO$_4$, for approximately 2 minutes. Appropriate portions of the brain were trimmed and placed on the ice-cold stage of a vibrating tissue slicer (Leica: VT-1000S). The stage was immediately filled with both oxygenated and frozen preparation buffers. The thickness of each tissue slice was 350 μm. Each slice was gently taken off the blade by a painting brush, trimmed, and immediately soaked in the oxygenated preparation buffer for 1 hour at room temperature. Then a slice was placed on the center of the MED probe. The slice was positioned to cover the 8×8 array. After positioning the slice, the MED probe was immediately placed in a box filled with 95% O$^2$ and 5% CO$^2$ and allowed to recover at 32° C. for 1 hour.

Electrophysiological Recording

During electrophysiological recording, the slices on the MED probe were placed in a small CO$_2$ incubator (Asahi Lifescience: model 4020) at 32° C. After recovery of the slice on the MED probe, the medium was replaced with DMEM/F-12 mixed medium without serum. The slices were on the interface, and contacted with a moisturized 95% O$_2$ and 5% CO$_2$ gas mixture. In this condition, the responses were recorded for more than 2 hours.

Drugs were purchased from RBI (diazepam, bicuculline, CNQX, 2-hydroxysaclofen) or Sigma (all other compounds). CX614 and CX691 were produced by Cortex Pharmaceuticals Inc. (Irvine, Calif.). All drugs were bath applied at known concentrations and were prepared daily from frozen aliquots.

Spontaneous and evoked field potentials at all 64 sites were recorded simultaneously with the multi-channel recording system (Matsushita Electric Industrial Co. Ltd, the "MED64 system") at a 20 kHz sampling rate. In the case of the evoked response, one of the planar microelectrodes out of the 64 available was used for cathode of stimulating. Bipolar constant current pulses (10 to 50 μA, 0.1 msec) were produced by the data acquisition software through the isolator. The stimulating microelectrode was selected by the 64 switch-box. The measured field potentials were then subjected to analysis using the CSD analysis (Nicholson et al) discussed below.

Current Source Density (CSD) Analysis

The well-studied methods of current source density analysis use the Laplacian transform ($\nabla 2$) on measured field potentials (φ) to attempt to identify the locations and relative magnitudes of current sources and sinks (Im) (Howland et al., 1955; Mitzdorf, 1985 for review):

$$Im = -(\sigma x \nabla 2x\phi + \sigma y \nabla 2y\phi + \sigma z \nabla 2z\phi)$$

where σ is the conductivity in each of the three orthogonal dimensions. The method is rarely used in its full three-dimensional form for electrophysiological measures (Nicholson, 1973; Nicholson & Freeman, 1975; Nicholson & Llinas, 1975) but rather a reduced form in one dimension is typically applied (Haberly & Shepherd, 1973; Ketchum & Haberly, 1993; Kolta et al, 1996). One-dimensional current source density analyses are, however, conducted in material of two or more dimensions (e.g., a brain slice), with the consequence that any currents occurring orthogonally to the axis of measure are undetected, and the resulting one-dimensional results may therefore be misleading. Care is thus taken in one-dimensional analyses to ascertain that there are minimal currents occurring laterally to the orientation in which samples are measured. Preferably, when the in vitro neuronal sample is a slice of the hippocampal region of the brain, alignment of the linear series of measures is made so as to be parallel to the direction of apical dendritic growth (as it has been demonstrated that currents lateral to apical dendrites are very small relative to currents occurring along the apical-proximal axis). The technique used in this Example is a two-dimensional method in which simultaneous samples are recorded from multiple electrodes in an equidistant array, enabling the continuous sensing of current flows in any direction within the plane of the slice, regardless of the relative orientation of the rows and columns of the array and the dendritic processes present in the slice. The array is made up of 64 planar electrodes, each with a size of 50×50 μm, arranged in an 8×8 pattern with interpolar distances of 150 μm or 450 μm (Oka et al., 1999).

After low pass filtering at 100 Hz, the data is spatially smoothed by a 3×3 weighted average kernel (0 1/8 0, 1/8 1/2 1/8, 0 1/8 0) and the result convolved with a 3×3 Laplacian kernel (0 1 0, 1 −4 1, 0 1 0) to produce a discrete approximation of the second spatial derivative. Preferably, the medium is considered ohmic with a homogeneous conductance. The full correlation matrix is computed for all channels (64) in the time window considered (0–3 sec). Current vs. time plots for single points in the slice is obtained by computing the 8×8 current source density for each time step, and calculating the value at the desired location via bilinear interpolation. Well-recognized limitations on the resolution affordable by current source density analysis arise from the relationship between the interelectrode distance (sampling resolution) and the radii of current sources or sinks occurring in the slice, and would be appreciated by one skilled in the art. The phenomenon of 'aliasing,' well known in the realm of computer graphics interfaces, refers to the occurrence of spurious data "ghosts" (aliases) when the distance between sampling points is larger than the size of the smallest phenomena to be represented. In computer screen graphics this occurs when the screen resolution is insufficient for the image being displayed (FIG. 1 left panel—A high-resolution image with smooth edges, FIG. 1 middle panel—The same image as sampled with relatively low-resolution inter-pixel distance appears to have new features with high spatial frequency (the-jagged stairsteps)). The appearance of spurious images on the screen is typically treated by 'anti-aliasing' that incorporates low-pass filtering of the image with introduction of partially shaded pixels at the image's edges (FIG. 1 right). Anti-aliasing includes a low-pass filter that removes the spurious alias features from the image, and therefore may also (as in the present instance) eliminate some high spatial frequency detail from the original image. The corresponding potential introduction of artifacts into array-sampled physiological data can be removed by the same anti-aliasing method (see FIG. 2 below), and will correspondingly eliminate some fine (high spatial frequency) detail from the data. Preferably, the analysis uses low-pass filtering without full antialiasing. Alternatively, if the data contain phenomena with spatial frequencies too high to be resolved by the interelectrode sampling distances, the result is low-pass filtered to remove spurious aliases while also removing high frequency data (FIG. 2).

Figure 2:
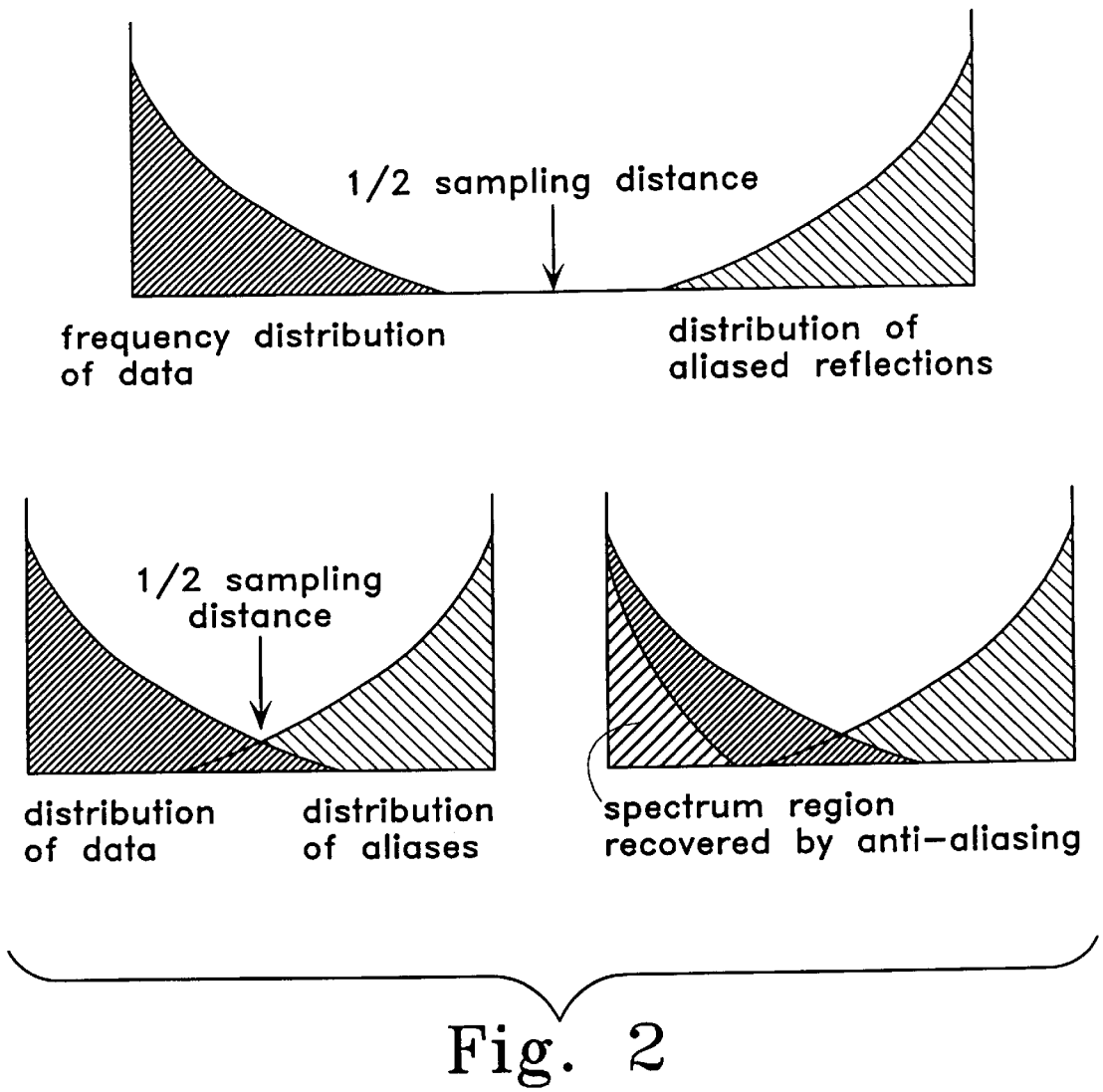
FIG. 2 depicts the effects of anti-aliasing.

Specifically, FIG. 2 depicts the effects of anti-aliasing. The top panel shows an instance of inter-sensor spacing sufficient for the resolution of the sampled data. Aliases appear as very high frequency features; low-pass filtering at one-half the inter-sensor spatial frequency (double the inter-sensor distance) eliminates all aliases without reducing resolution of the sampled data. On the other hand, the bottom left panel in FIG. 2 shows the instance in which the inter-sensor spacing was insufficient for the resolution of the sampled data. Spatial frequency of aliases overlap the highest frequencies present in the data. The left panel shows that low pass filtering at one-half inter-sensor spatial frequency will fail to eliminate all the aliases, and yet will eliminate some of the finest detail of the data. The right hand panel in FIG. 2 shows that low pass filtering at a lower spatial frequency successfully eliminates all spurious aliases, and further reduces the resolution of the sampled data, eliminating much of the high-frequency fine detail that may be present in the measured data. Only lower frequency or larger events remain.

Results

Continuous, Two-dimensional, Current Source-density Analysis

Figure 3A:
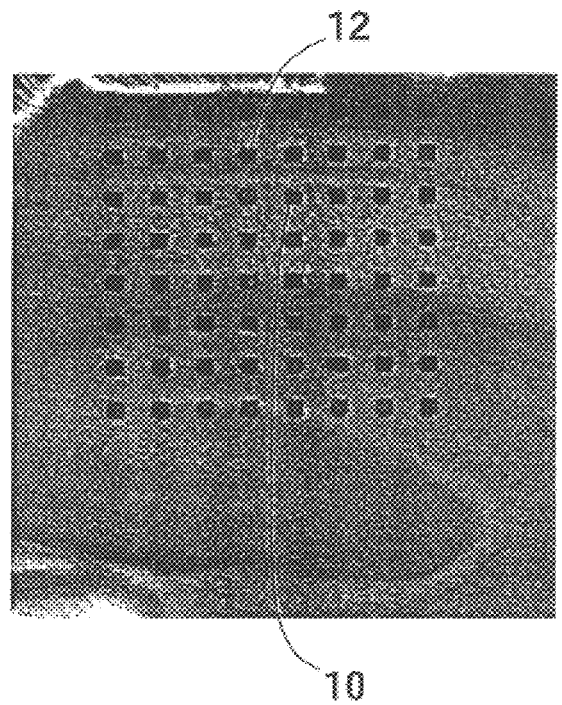
FIGS. 3A and 3B show respectively the placement of a hippocampal slice on an 8×8 detector array and an elicited post-synaptic response at one of the electrodes.
Figure 3B:
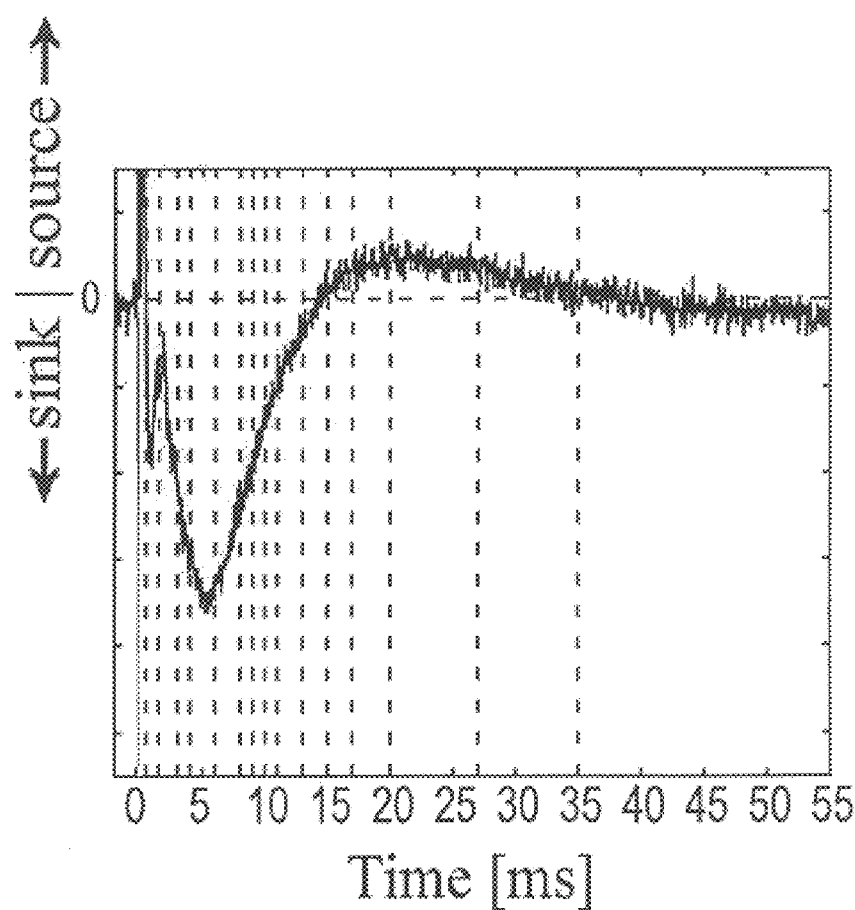

Two-dimensional current source density analyses were conducted in the context of stimulation of the Schaffer-commissural afferents to field CA1 in a hippocampal slice preparation. FIGS. 3A and 3B illustrate a typical experiment. FIG. 3A shows the placement of the slice on an 8×8 MED electrode array, with interelectrode spacing of 150 $\mu$m, centered in the apical dendritic field of CA1 in a hippocampal slice. The electrodes cover the basal dendrites of CA1, apical dendrites of CA1, and the upper blade of the dentate gyrus granule cell field. on the electrode array. To prevent the GABAA-and GABAB-mediated inhibitory components, this experiment was carried out with 50 $\mu$M picrotoxin and 100 $\mu$M 2-hydroxysaclofen. FIG. 3B shows a typical postsynaptic current elicited (EPSC) by a single stimulation pulse to the electrode indicated in dark gray (10) and measured from the electrode in light gray (12). The time scale is typical for such evoked responses. Vertical dotted lines mark the time points for which measures will be taken across all 64 electrodes and shown in FIG. 4 below.

FIG. 3B illustrates the time course and magnitude of the postsynaptic current at the indicated electrode, which is in the proximal portion of the apical dendrites of CA1. The direction of the current sink and source are as indicated; after the initial fiber volley (lasting approximately 1 msec) a current sink increased over a period of about 5 msec and decreased over the subsequent five milliseconds before returning to baseline at roughly 13 msec. It became a current source and lasted for approximately another 15–20 msec before returning to baseline at about 35–40 msec. The relative magnitudes and time courses of the sink and source are typical for such evoked responses.

Figure 4:
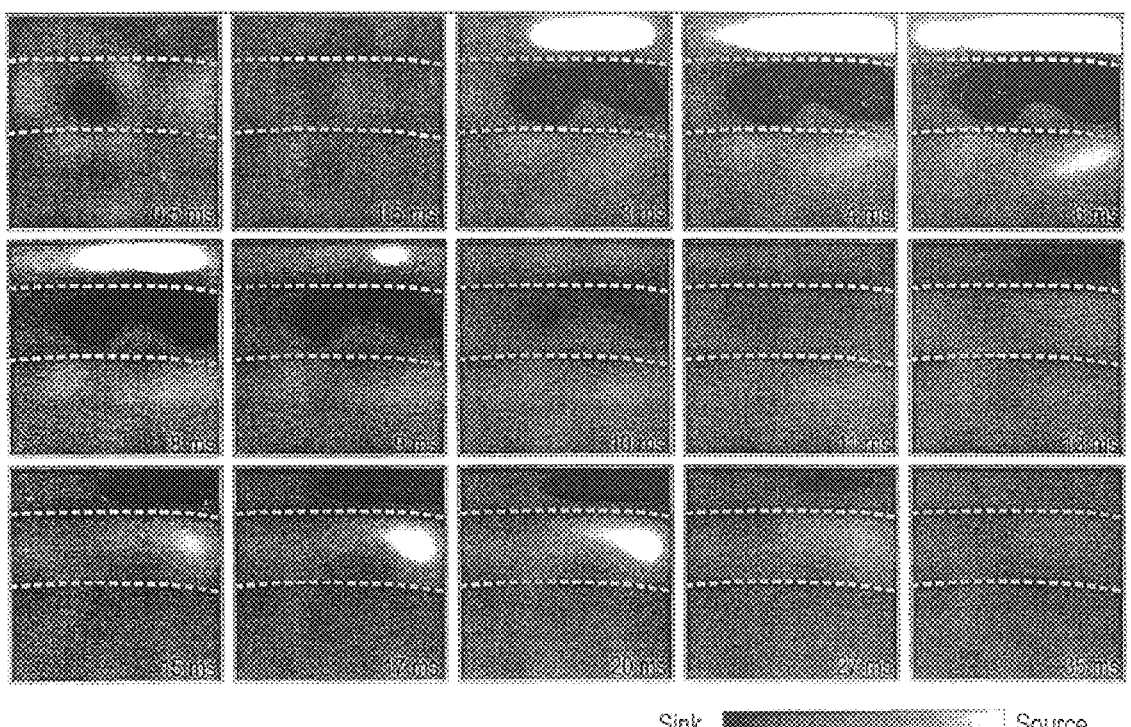
FIG. 4 shows a continuous two-dimensional current source density analysis of evoked response computed from the placement of the slice in FIGS. 3A and 3B.

Two-dimensional current source density analysis was performed to obtain comparable measures of current sources and sinks of the same response. FIG. 4 illustrates the continuous two-dimensional current source density analysis of the evoked response shown in FIG. 3B. Each panel in FIG. 4 illustrates the computed instantaneous sources and sinks in the slice, at selected times indicated by vertical dashed lines in FIG. 3B. The array was positioned on the slice as shown in FIG. 3A; the cell body layer of hippocampal field CA1 defines a roughly horizontal curve about one quarter of the way from the top of each panel. The dotted lines indicate the cell body layer of CA1 (top) and the most distal extent of the apical dendritic field (bottom). As seen in the calibration bar at bottom, sinks are black and sources are white, against a current-neutral background of gray.

It can be seen that after the initial fiber volley (lasting roughly 1 msec), a current sink in the apical dendrites of CA1 rapidly rose over a period of approximately 5 msec (see panel marked '6 ms') and fell over the subsequent five milliseconds before disappearing at about the 11 ms panel with the singularity appearing at the site of stimulation. After an interim of about two milliseconds during which currents were indistinguishable from neutral background, a source appeared in the apical dendrites ('15 ms') and lasted for approximately another 15–20 milliseconds before disappearing at roughly 35 ms. The time courses and magnitudes of the waveform from a single electrode (FIG. 3B) can be seen to correspond closely to the computed current source density sink-source series in FIG. 4.

Revealed by the two-dimensional current source density method are spatial aspects of the current sources and sinks that are difficult to discern by other means. The excitatory postsynaptic current sink spread across the apical field of CA1, in the region of Schaffer commissural fibers presumably stimulated by the initiating current pulse (panels from 3 ms to 9 ms); the ensuing current source occupied approximately the same zone (panels 15 ms to 27 ms). Both the sink and subsequent source that occurred in the apical dendrites were accompanied by currents of reversed polarity in the basal dendritic field of CA1 (near the top of each panel). Thus the predominant evoked response can be characterized as a current sink-source dipole that occurred from 3 to 9 msec and reversed to form a current source-sink dipole from 15 to 27 msec. Other, smaller currents were present in the slice but are not discussed here.

After a brief pause, a current source appears in these dendrites, with its center slightly more distal than that of the current sink. The apical source intensifies, expands, dissipates and disappears by about time 50 msec, making the 'period' of the evoked response about 50 msec. Both the apical sink and ensuing apical source are accompanied by a field of reversed polarity appearing in the basal dendrites of CA1 (top of each panel) that grows and dissipates with approximately the same time course as the apical events.

As described, the anti-aliasing performed in these analyses to prevent the introduction of artifacts due to aliasing will cause a loss of data with sufficiently high spatial frequencies. The filtering passes only those phenomena with spatial frequencies at most one-half that of the sampling frequency; in the present Example the inter-electrode distance was 150 $\mu$m, preventing the measurement of current sources or sinks smaller than about 300 $\mu$m across (150 $\mu$m radius). This could be a shortcoming in a structure the size of hippocampal field CA1, and it is expected that fine spatial detail is lost in the method. It is instructive, therefore, to examine the spatial resolution of the CSDs measured by this method.

Figure 5A:
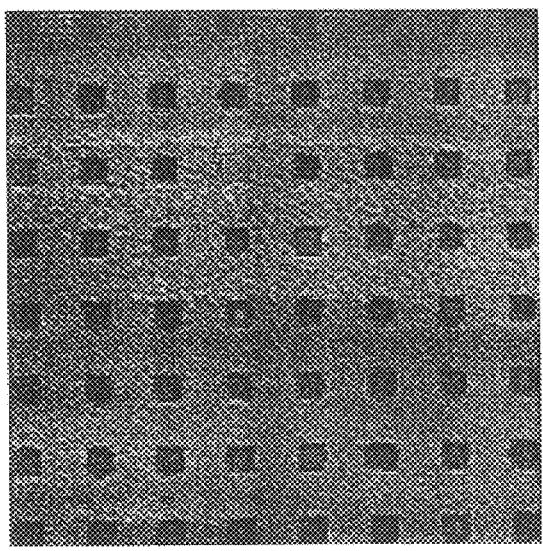
FIGS. 5A and 5B show the alignment of computed physiological phenomena with a known anatomical structure.
Figure 5B:
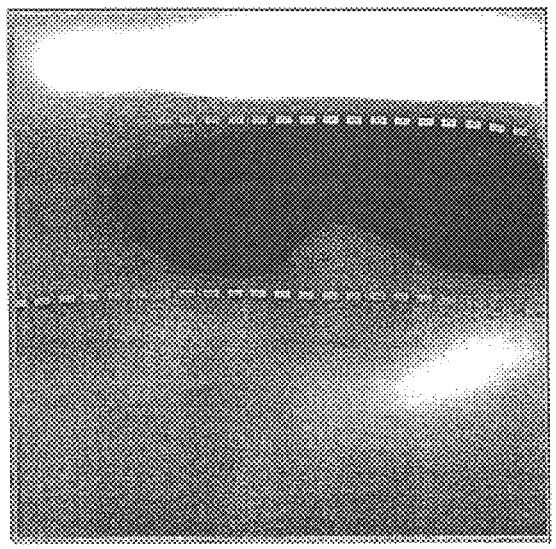

FIGS. 5A and 5B depict the boundaries of the apical dendrites of field CA1 superimposed on the region of measurement.

FIG. 5A shows the slice and the position of the array (from FIGS. 3A and 3B); on the right is the instantaneous CSD in the region of the electrode array (from FIG. 4), at 6 msec after stimulation at the indicated electrode. The top of the array coincides with the basal dendrites of CA1; the upper-central portion of the array overlays the field of apical dendrites in CA1, and the bottom third of the array overlays the upper blade of the dentate gyrus. The dotted lines indicate the cell body layer of CA1 (top) and the most distal extent of the apical dendritic field (bottom).

As seen in FIG. 3B, The primary measured current sink (black) occupies only the region where apical dendrites occur, and the reciprocal current source (white, top) occurred only in the region of basal dendrites. (An absence of current appeared in the computed image at the location corresponding to the stimulating electrode; no recordings were taken from that electrode and the resulting CSD processing left a gap.) The physiological response computed by continuous two-dimensional current source density analysis 6 milliseconds after the stimulation of a single electrode (indicated in dark gray); the image is a closeup of the 6 millisecond frame from FIG. 3B. Indicated are the limits of the apical dendritic field of CA1 by dotted lines. It can be seen that the extent of the evoked current sink closely corresponds to the limits of the apical dendrites. An apparent hole in the current sink occurs at the site of the stimulating electrode, where no recording is performed and no current source density is computed. There is little current in the cell body layer itself, and current source appears in the basal dendrites (top of panel). There is little current at the apical tips of the CA1 dendrites (middle of panel) and some less intense current sources occurring in the apical dendrites of the granule cells of dentate gyrus.

It can be appreciated that the borders of the computed sink do not coincide precisely with the location of the anatomical limits of the dendritic field, inaccuracies that may result from the resolution limits of the method.

Distribution and Current Sources for Carbachol-induced Beta Waves Within the Hipiocampus FIG. 6A contains a micrograph of a hippocampal slice and an underlying 64 electrode array with 450 μm between recording positions (the 'broad array'). Subfields of hippocampus and overlying cortex may also be seen. FIG. 3B shows spectra of carbachol-induced spontaneous activity at 20 electrode sites that contact part of hippocampus in the slice. Each x-axis is on a logarithmic scale from 1 to 100 Hz. Activity is seen in the 10–30 Hz frequency range, especially in apical dendrites of fields CA1 and CA3, with lower levels of activity elsewhere. The calibration bar is $5 \times 10^{-11}$ $V^2$. As is seen in FIG. 3C, the baseline activity was of low voltage and generally devoid of activity and there were no reliable differences between subfields.

Figures 6C, 6D, 6E:
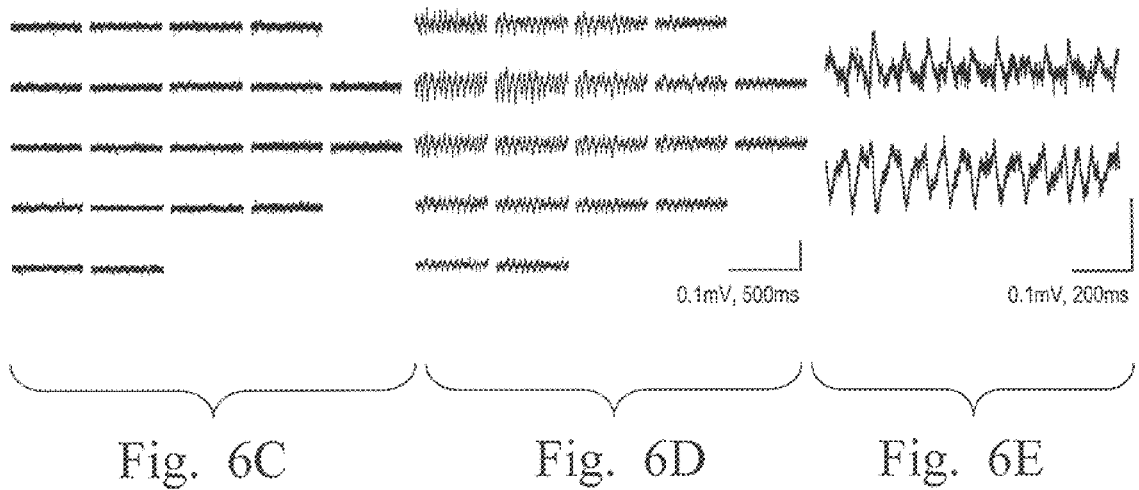

Infusion of carbachol was followed by a gradually developing rhythmic activity in fields CA1 and CA3 that was close to or within the beta band (10–30 Hz) in 41 of 55 slices tested (FIG. 6D for an example). Thirty four out of the forty one slices had beta band oscillations in field both CA1 and CA3. Low voltage activity at the upper end of the theta range was observed in field either CA1 or CA3 in the remaining seven cases. The relative prominence in CA1 vs. CA3 was not consistent across slices. high frequency activity was also found in the dentate gyrus, much more so in the internal than external wing of the structure (FIGS. 6B, D). FIG. 6E shows a closeup of carbachol induced activity in the upper left electrodes in the array, indicating the reversal of polarity across the cell body layer of field CA1. In FIG. 6E, the calibration bars are 0.1 mV; 250 msec. As may be seen in the higher gain record of FIG. 3E, in the pyramidal cell fields, the waves were larger in the apical than in the basal dendrites and typically had phase reversals between the two loci.

Fast Fourier transforms were used for quantitative analysis of the frequency and distribution of the carbachol induced rhythms. For the example illustrated in FIG. 6B, most of the power in the spectrum was found between 10 and 30 Hz with a definite peak at 20 Hz. The group mean for the dominant CA1 frequency for all slices was 18.8±5.7 Hz (mean ± s.d.) and 19.2±4.8 Hz for the beta instances alone. The equivalent values for CA3 were 16.4±5.7 and 17.3±4.2 Hz. The differences between CA3 and CA1 did not reach statistical significance. The recording sites with the greatest power in the 10–30 Hz band were located in the apical dendrites of field CA3 and CA1, typically in the more distal fields.

As may be seen in FIG. 7A, arrays with 150 μm spacing (the 'dense array') provided finer spatial resolution of the rhythmic activity. Recording centered on the CA3 /CA1 border revealed a surprisingly steep gradient of absolute potentials in the distal to proximal dimension with the largest potentials occupying a discrete region corresponding to stratum moleculare of fields CA3 a and CA3 b (FIG. 7B). It is noteworthy that potentials reversed across the cell layer boundary (see, e.g., upper left quadrant of FIG. 7B). Lesser though still substantial voltage bands are also present in CA1. The frequency spectra for all channels are shown in FIG. 7C.

Figure 8:
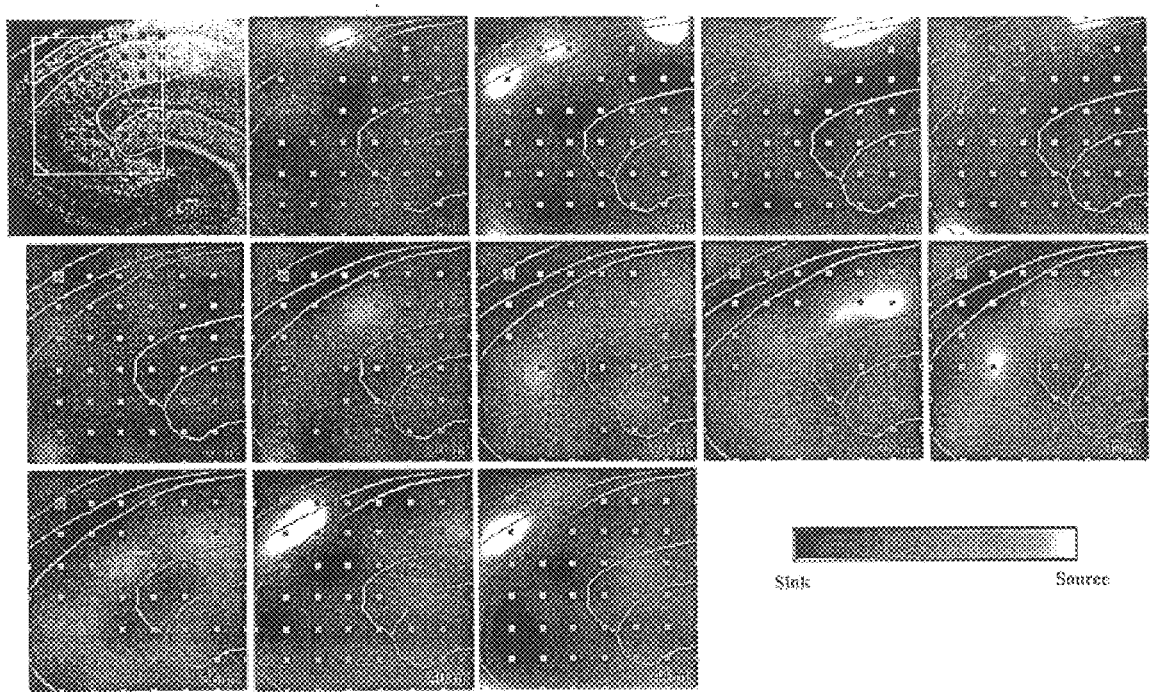
FIG. 8 shows a current source density analysis of carbachol-induced activity for the slice shown in FIG. 7A.

Continuous two-dimensional current source density analyses were conducted to further define the sources of these cholinergically induced oscillations. FIG. 8 illustrates the instantaneous sources (white) and sinks (black; against a neutral background of gray), at 4-millisecond intervals from an arbitrarily chosen starting time of 0 during the same spontaneous activity a dense array shown in FIG. 7. The outlines of the granule and pyramidal cell fields of CA3 and CA1 and the extents of their apical dendrites are superimposed to illustrate the locations of events occurring during the time period. The array includes part of the upper blade of the dentate gyrus. Each frame shows the instantaneous computed current source density in the region of the electrode array. From an arbitrarily chosen starting point, a sink appears in the apical dendrites of the border between fields CA3 and CA1, with an associated source across the cell boundary layer in the basal dendrites. A large sink in apical CA1 is accompanied by a source in the basal dendrites of CA1. The sink and its accompanying basal source intensified and expanded over the course of roughly 12 milliseconds, and both subsided to approximate baseline levels by roughly 16 msec after initial appearance. After a brief interim during which activity is not distinguished from background, a source appears in the apical dendrites at about 20 msec, with a corresponding sink in the basal dendrites. These expand and intensify before dissipating by roughly 20 msec later (40 msec), after which an apical sink reappears to re-initiate the cycle. The source (and its accompanying dipole) lasted for roughly 20 msec before dissipating. It is noteworthy that the apical source appeared to have its center more distally located than that of the more focal apical sink which preceded it, to within the resolving power of the interelectrode spacing of 150 μm. The sink-source dipole recurred and gave rise to the frequency plot shown in FIG. 7C; the time course from peak to peak of this recurring apical sink-source dipole was approximately 40 msec, consistent with a frequency of ~25 Hz.

FIGS. 9A and 9B show a typical record of the repetitive oscillations induced by carbachol in a slice. The source-sink and sink-source dipoles, and their sharply defined boundaries between sources and sinks along the pyramidal cell body layer of the in vitro neuronal sample, were recurring features across many experiments, as was the latency from one apical sink through an apical source to the next apical sink FIG. 9A shows a hippocampal slice on a broad (450 μm interelectrode spacing) array. The electrodes used to measure basal dendritic responses of pyramidal cell fields are indicated in light gray; those used to measure apical dendritic responses are in dark gray. FIG. 9B shows averaged responses from apical (black) and basal (light gray) dendritic fields are shown over 500 msec (0.5 second) of elapsed time for the slice in FIG. 9A. Carbachol-induced (20 μM) oscillations were sustained across all sampled periods, as in this typical response. Average apical and basal responses are reversed in polarity; i.e., are 180 degrees out of phase. The sustained occurrence of alternating current source-sink dipoles across the cell body layers of CA3 and CA1, within the range of 10–30 Hz (beta), were robustly observed in the majority of slices and time periods sampled.

Shifts between sinks and sources over larger areas were assessed with continuous two-dimensional current source density analyses using an electrode array with interelectrode spacing of 450 μm, as opposed to previous current source density examples, which used arrays of 150 μm distances. The resulting aliases and antialiasing (see FIG. 2) necessarily entailed a further loss of resolution; for interelectrode spacing of 450 μm and concomitant antialiasing, the smallest events that can reliably be imaged are those with a radius of 450 μm (diameter of 900 μm) or larger.

Figure 10:
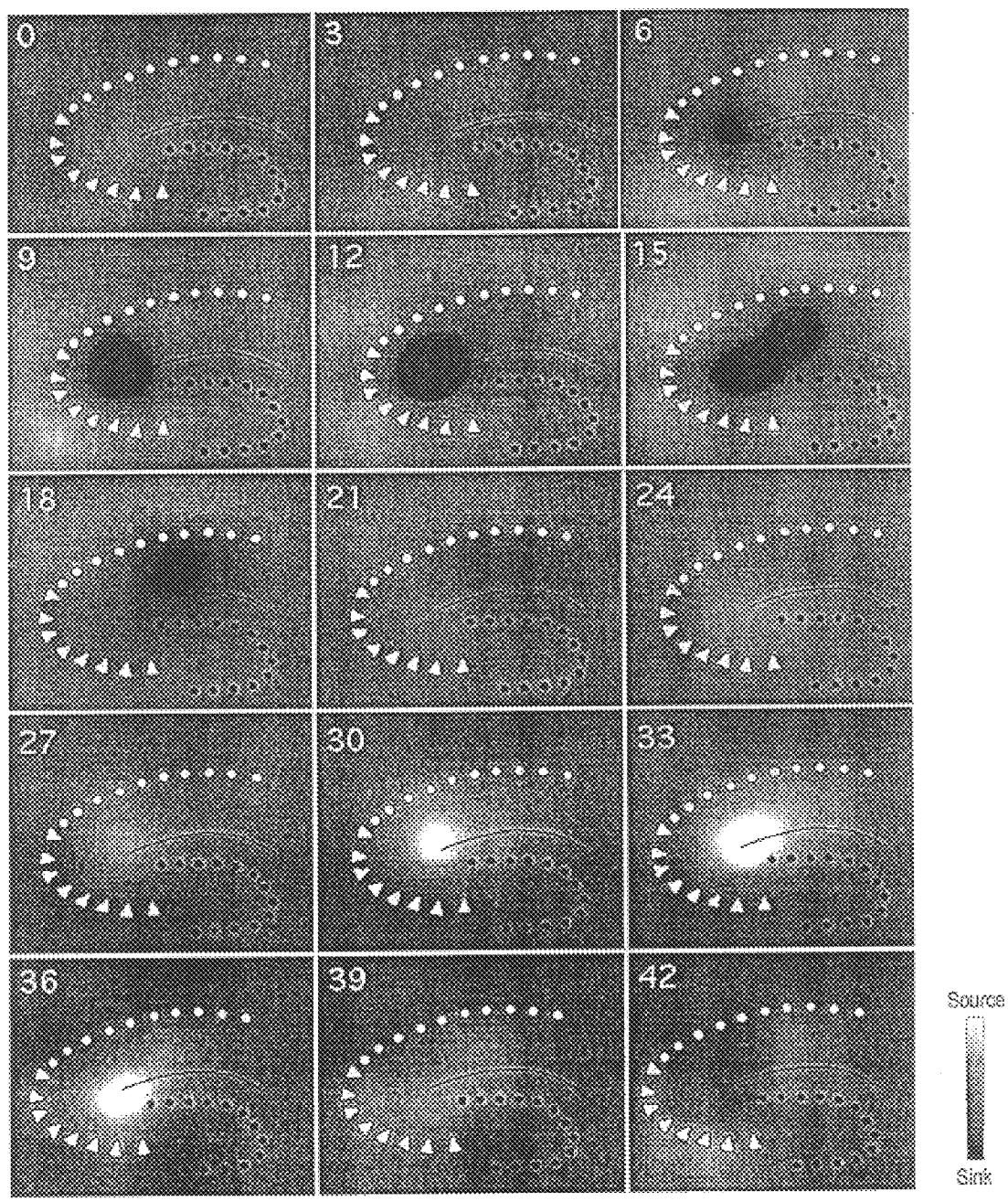
FIG. 10 shows a computed evolution of current source density over a specific time.

FIG. 10 shows the computed evolution of current source density over 42 msec. Each frame shows the computed current source density at a particular time (indicated in milliseconds in the upper left corner of each frame) during recording of spontaneous activity with a broad (450 μm spacing) array. Black indicates maximum magnitude of sinks; white indicates maximum magnitude of sources. The positions of the pyramidal and granule cell fields are indicated.

Beginning at an arbitrarily chosen time 0 msec, a weak current source in the apical dendrites of field CA3 is surrounded by diffuse sources centered on the pyramidal cell layers. An intense focal sink in the apical dendrites or proximal s.radiatum of field CA3 begins at about 6 msec, accompanied by sources in the cell and basal dendrite layers of CA3. The sink grew and a fully developed sink-source relationship centered on CA3 b was evident at the 9 msec time point. The sink continues through roughly 12 msec before beginning to expand toward field CA1. The sink in apical CA3 dissipates at roughly 18 msec, followed about three msec later by the apical sink in CA1 and was accompanied by the appearance of a pronounced cell body/basal dendrite source at 15 msec. Note that by this time point the sink-source relationship in CA3 had begun to collapse. The basal sources dissipate at roughly the same time as their associated apical sinks. An apical source begins in CA3 at about 24 msec, accompanied within a few milliseconds by a mild basal source in CA3; the apical source then expands towards CA1, with an accompanying basal sink in CA1. These source-sink pairs then dissipate after about 15–20 msec. Such cycles recur irregularly in this slice. The wave involved an intense apical dendritic sink lasting about 10 msec followed by an apical source lasting for about twice that period. These events began in CA3 and were seen in CA1 within 3–5 msec. In summary, cholinergically induced beta range rhythms have current sources that are located in the apical dendrites and that are usually better defined than the more proximally situated current sinks.

These observations showed that relatively brief apical sinks are interposed between the longer lasting apical sources. Examination of averaged currents demonstrated that distribution of sources and sinks across the pyramidal cell subdivisions of hippocampus varied between slices. Between-slice variability was also present in serial current source density analysis with major differences in the degree to which events were centered in CA3 vs. CA1. However, the brief apical sink—longer apical source sequence for the apical dendrites was prominent in all slices exhibiting oscillations in the beta range.

Carbachol Induces a 40 Hz Rhythm in Retrohippocampal Cortex.

Figure 11A:
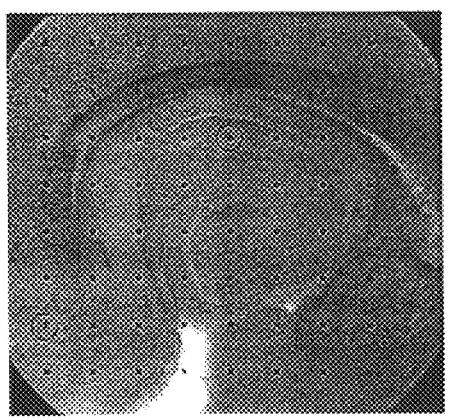
FIG. 11 shows two distinct carbachol-induced rhythms in hippocampus and cortex.
Figure 11B:
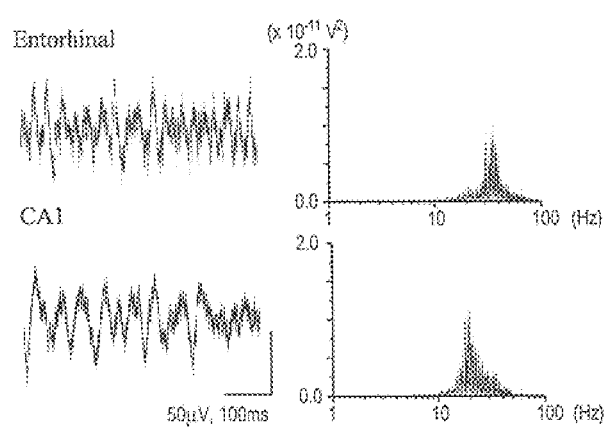
Figure 11C:
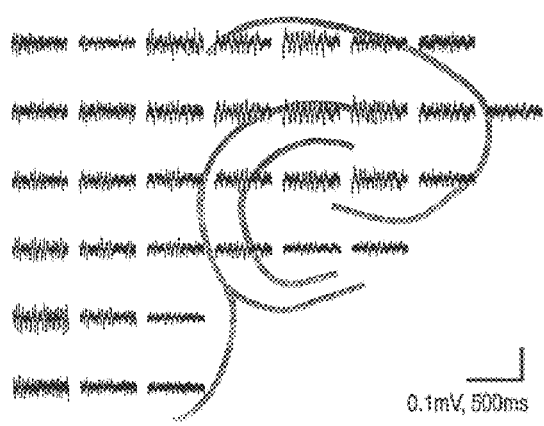
Figure 11D:
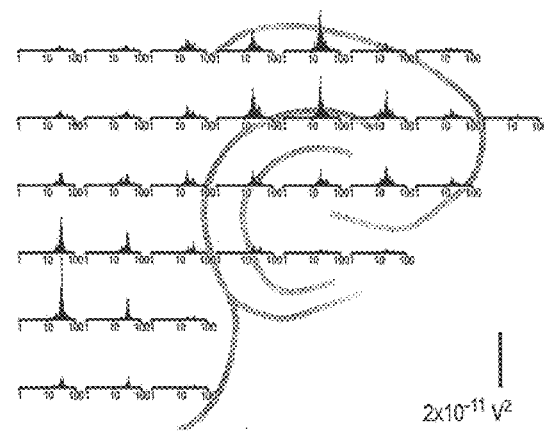

The question of whether the rhythms elicited by carbachol are regionally differentiated was addressed by close examination of those slices in which the electrode array was positioned underneath a significant portion of the retrohippocampal cortex field along with the pyramidal cell fields of hippocampus itself. FIG. 11A shows a micrograph of a cortico-hippocampal on a broad array. Two sites of interest—one in the CA1 (100) and one in the deep layer of the entorhinal cortex (102) are shown. Carbachol (50 μM)-induced fast waves from the indicated positions in field CA1 and entorhinal cortex are compared in FIG. 11B. Power values are given in the drawing as times $10^{-11}$. As may be seen in FIG. 11B, the entorhinal oscillations have a higher frequency than those from the hippocampus. Fast Fourier transforms indicated that the dominant frequency in the cortex is about twice that in field CA1. Rhythmic activity with a peak near 20 Hz was found through the apical dendrites of the hippocampal pyramidal cell fields while the 40 Hz activity was predominantly associated with the entorhinal sites. It was also observed that the 40 Hz oscillations were centered in the deep layers of the medial entorhinal cortex (right top spectrum in FIG. 11B). Regions lying between the hippocampus and medial entorhinal cortex exhibited both peaks. Indeed, it appears the relative balance of 40 vs. 20 Hz increases in an orderly manner across the series of steps included in the retrohippocampal cortex. Forty Hz activity was recorded in the deep layers of the entorhinal cortex in each of the 15 slices which had appropriately positioned electrodes; it thus appears to be a characteristic response of this region to cholinergic stimulation. Results for all recording sites are summarized in FIGS. 11C (distribution of representative activity in the slice (calibrations bar: 0.1 mV, 500 msec.)) and FIG. 11D (distribution of low-pass (0–100 Hz) filtered power spectra in the slice (Calibration bar: $2 \times 10^{11}$ $V^2$)).

Transmitter Systems Involved in Carbachol Induced Beta Waves.

Carbachol-induced high frequency rhythms were completely eliminated by 20 μM atropine and greatly reduced by the AMPA receptor antagonist CNQX (20 μM). In the presence of bicuculline (10 μM), muscarinic stimulation produced high frequency spiking in the stratum pyramidale and in some instances epileptiform discharges, but rhythmic activity was absent. Under these conditions, carbachol initiated repetitive bursting behavior and occasional seizures. The interval between the epileptiform bursts sometimes approximated the period of the theta wave (data not shown). These seizures were similar to the activities reported by Williams and Kauer (1997).

Orthodromic Activation of Pyramidal Cells Triggers Beta-like Activity in the Apical Dendrites.

How the GABAergic cells responsible for apical sources are activated is clearly of importance for understanding the origins of beta oscillations. If pyramidal cell collaterals are involved, then orthodromic stimulation sufficient to cause repetitive spiking should result in the appearance of beta like activity in the areas in which the carbachol-elicited rhythms are found. Single pulse stimulation of the Schaffer-commissural fibers does not typically cause repetitive spiking because (i) the potent feed-forward dendritic inhibition in the stratum radiatum shunts the excitatory current and (ii) perisomatic inhibition prevents repetitive discharges. Concentrations of bicuculline that partially block the GABAa receptor pool were used to reduce these-inhibitory responses and thereby allow the pyramidal cells to emit 4–5 spikes in response to orthodromic stimulation.

Figure 12A:
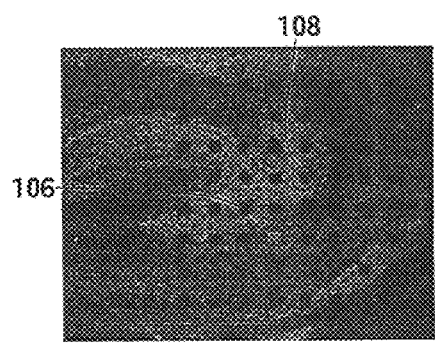
FIG. 12 shows a two-dimensional current source density analysis of betalike activity elicited by orthodromic activation of field CA3.
Figure 12B:
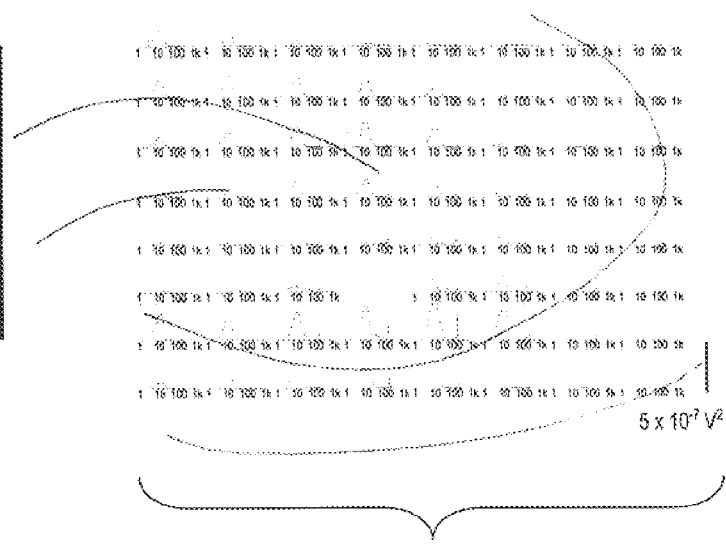
Figure 12C:
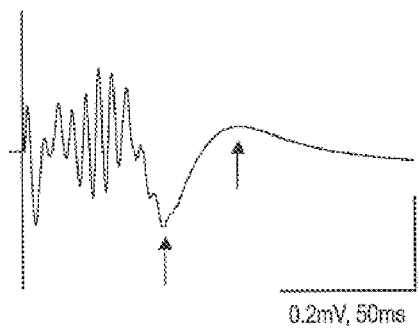
Figure 12D:
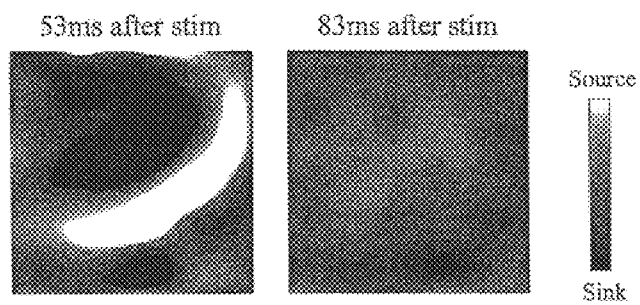

FIGS. 12A–12D show a two-dimensional current source density analysis of beta-like activity elicited by orthodromic activation of field CA3. FIG. 12A shows the position of the array (150 μm interelectrode spacing) with respect to a hippocampal slice, centered in field CA3. Stimulation was induced at the electrode indicated by solid color (106) and was recorded at the circled electrode (108). As noted below, FIG. 12B shows a typical response to orthodromic stimulation of field CA3. The response exhibits a small burst of spikes followed by a positive-going wave lasting approximately 30–40 msec. Arrows indicate the peak sink (53 msec) and peak source (83 msec). FIG. 12C shows the distribution of power spectra in the slice: the largest responses are in apical dendrites of CA1 and apical and proximal dendrites of CA3. Fourier transforms showed that the frequency spectrum for the response had peaks at 15–20 Hz and at 100–200 Hz (FIG. 12C); note that the log scale used extends from 1 to 1000. FIG. 12D shows a two-dimensional instantaneous current source density analyses at two time points (53 msec and 83 msec after stimulation, indicated by arrows). The 15–20 Hz component was pronounced in the distal apical dendrites and had a distribution similar to that for carbachol-induced beta waves. At 53 msec, the evoked current sink is at its peak, and can be seen to occur predominantly in the apical dendrites of CA3, with a corresponding source in the basal dendrites. At 83 msec, the rebound source peaks; it can be seen also to occur in the apical dendrites of CA3, with a corresponding sink in the basal dendrites.

Responses of the type described in FIG. 12B were sensitive to bicuculline concentrations and were blocked by it at 20 μM. Current source density analyses of the late evoked response showed a source that ran in the stratum radiatum about 200–400 μm above the s. pyramidale from the stimulation site near the hilus towards CA1; this was paralleled by a dense sink in the cell bodies and basal dendrites (FIG. 12D).

Benzodiazevine Identification and Characterization

Figure 13C:
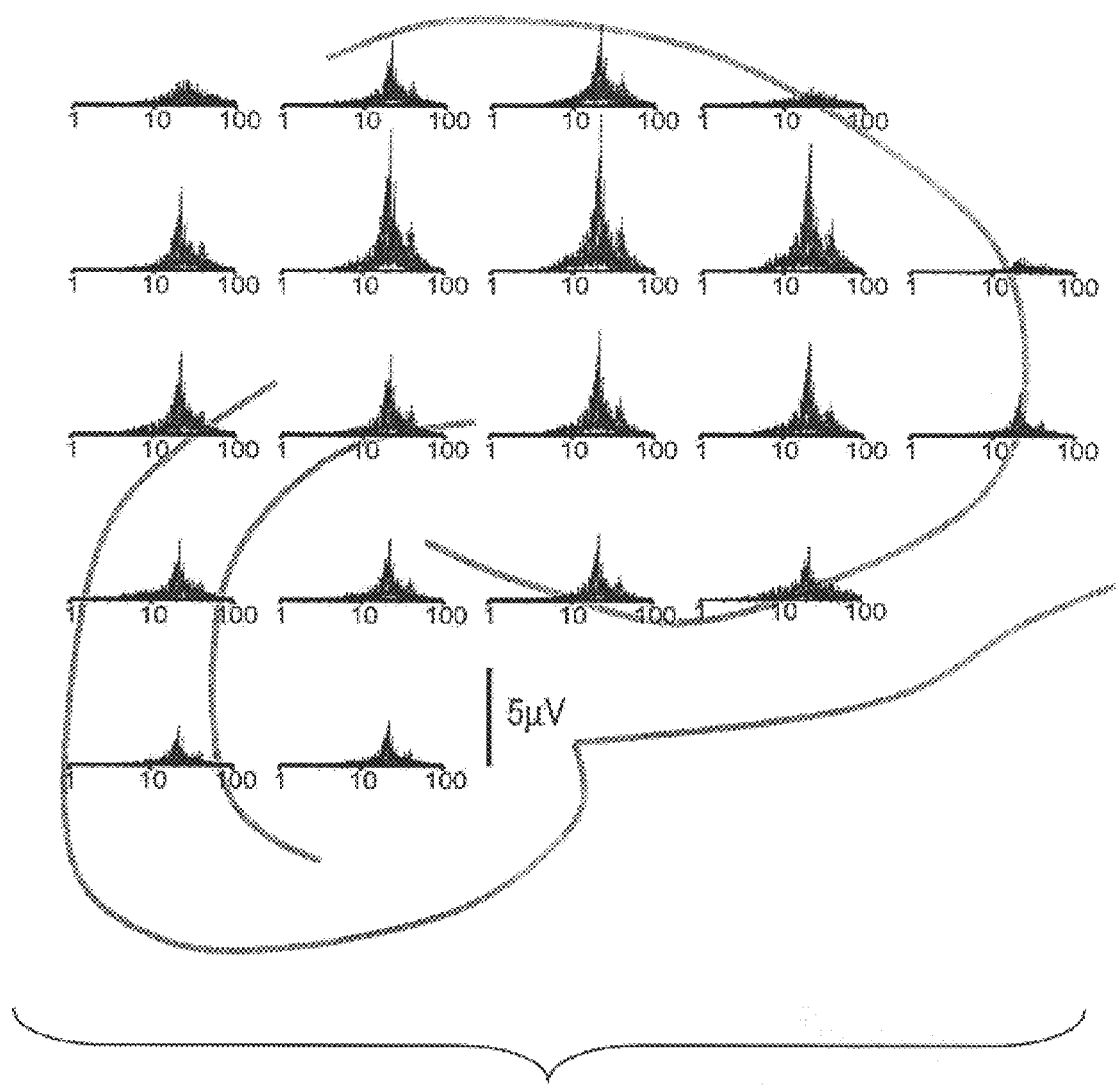
FIG. 13 shows the effect of benzodiazepines on carbachol-induced beta waves.

FIGS. 13A–13C show the effect of benzodiazepines on carbachol-induced beta waves. Benzodiazepines markedly enhanced the amplitude of beta oscillations as can be seen in a comparison of FIGS. 13A (20 μM carbachol alone) and 13B (same slice with carbachol plus 3 μM diazepam). A Fourier transform indicated that the increased amplitude was not accompanied by a significant change in the frequency of the waves. Rhythmic activity is greatly enhanced and spreads to regions that were relatively inactive. (Calibration bars for FIGS. 13A and 13B: 0.2 mV, 500 msec).

FIG. 13C summarizes the frequency spectra for recording loci within the hippocampus and shows the superposition of power spectra in the absence (black) and presence (gray) of diazepam. This showed that diazepam (gray spectra) caused a nearly threefold increase in power within the 20 Hz band over carbachol alone (black spectra), without much shift in the frequency. In addition, a peak is added at a higher (approximately 40 Hz gamma) frequency by the addition of diazepam. (Calibration bar: 5 μV).

Further, Table 1 summarizes the results for 8 experiments in which carbacholythms induced high frequency rhythms were present prior to the infusion of diazepam. The increase in power at peak frequency was 321±170% for CA3 and 217±137% for CA1. Within-slice effects of diazepam were correlated (r=0.93) and the increase in CA3 was statistically grater than that in CA1 (p<0.05, paired t-test, 2 tails). The frequency of the oscillations after diazepam was correlated across slices with that recorded under carbachlone (CA3: r=0.85; CA1: r=0.96).

TABLE 1

Summary of eight experiments in which carbachol-induced high frequency rhythms were present in a hippocampal slice prior to infusion of diazepam. Shown are the maximal percent increases in power at the peak frequency in fields CA3 and CA1.

| Slice # | CA3 (%) | CA1 (%) |
| --- | --- | --- |
| 1 | 639 | 521 |
| 2 | 344 | 264 |
| 3 | 414 | 211 |
| 4 | 197 | 119 |
| 5 | 431 | 200 |
| 6 | 177 | 213 |
| 7 | 132 | 117 |
| 8 | 235 | 90 |
| mean ± sd | 321 ± 170 | 217 ± 137 |

As seen, the cation of a member of the benzodiazepine class of compounds markedly enhanced the amplitude of beta oscillations. For the results shown in FIGS. 14A–C and 15A–C, the potentials were measured for the respective samples with carbachol alone and with carbachol plus two type benzodizepines: one example being 3 μM diazepam (FIGS. 14A–C) and another being 20 μM flurazepam (FIGS. 15A–C).

Figure 14A:
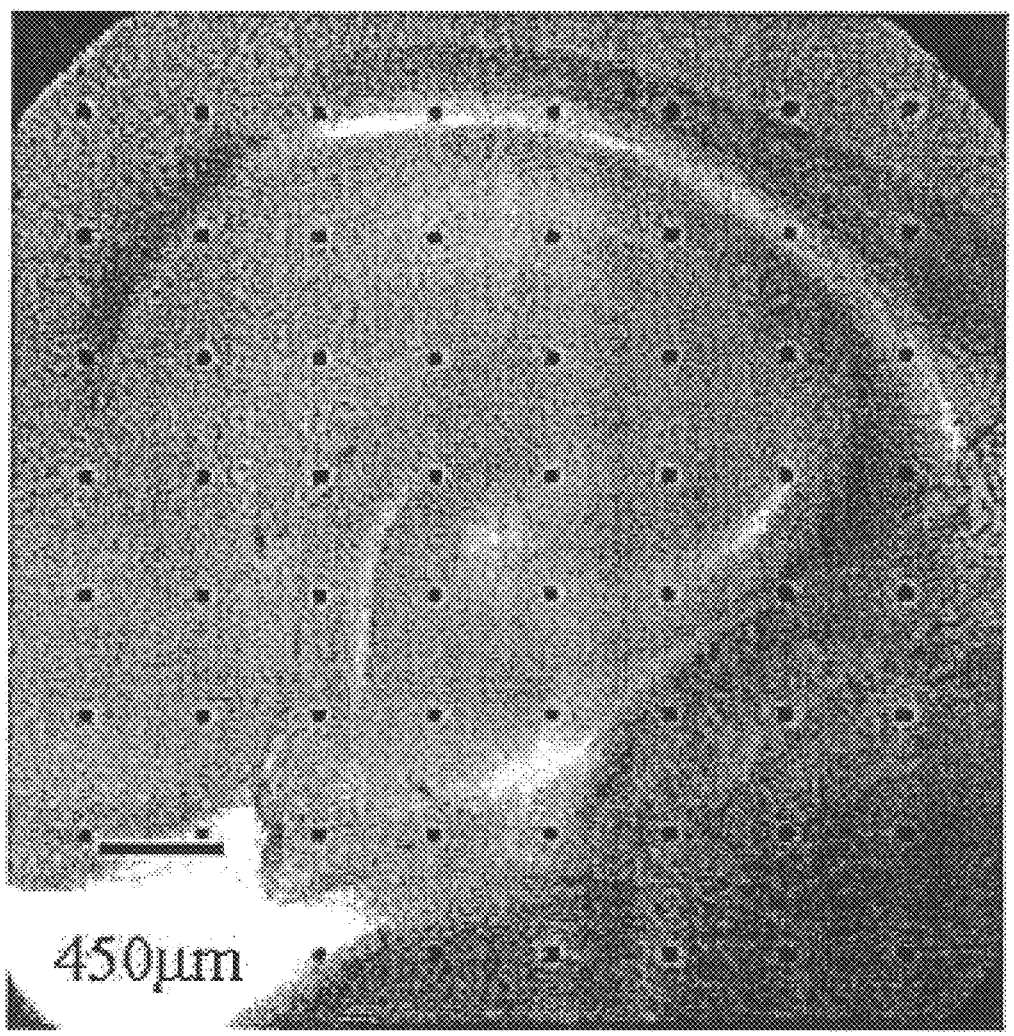
FIGS. 14A–C show the effect of diazepam on carbachol-induced beta waves.
Figure 14C:
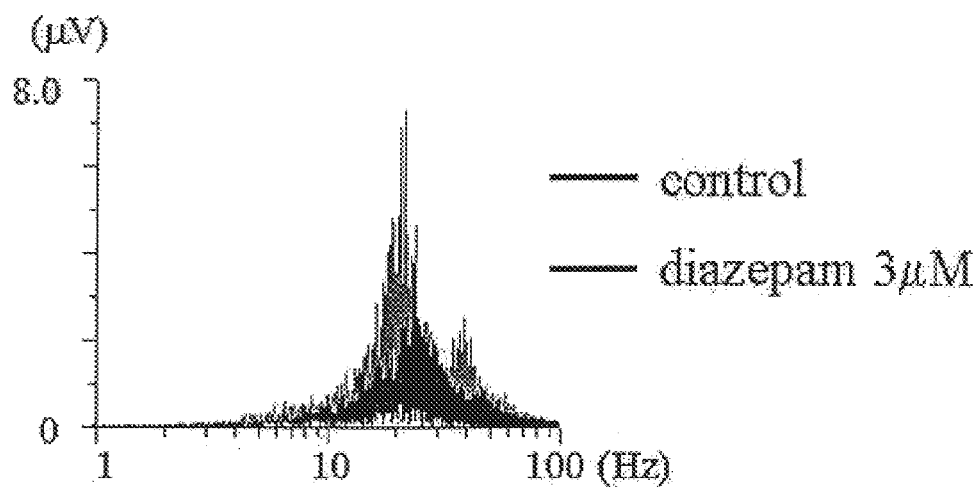
Figure 14B:
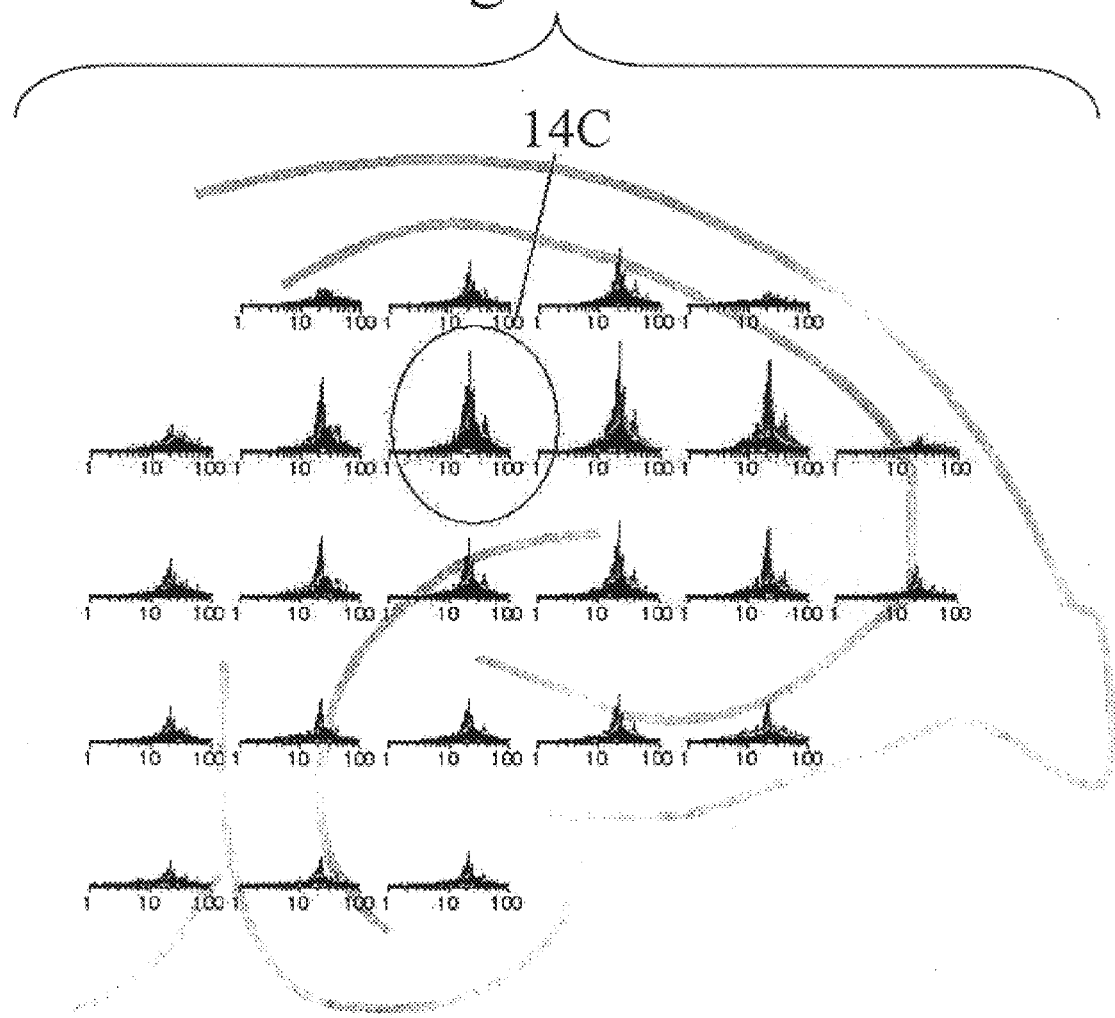
Figure 15A:
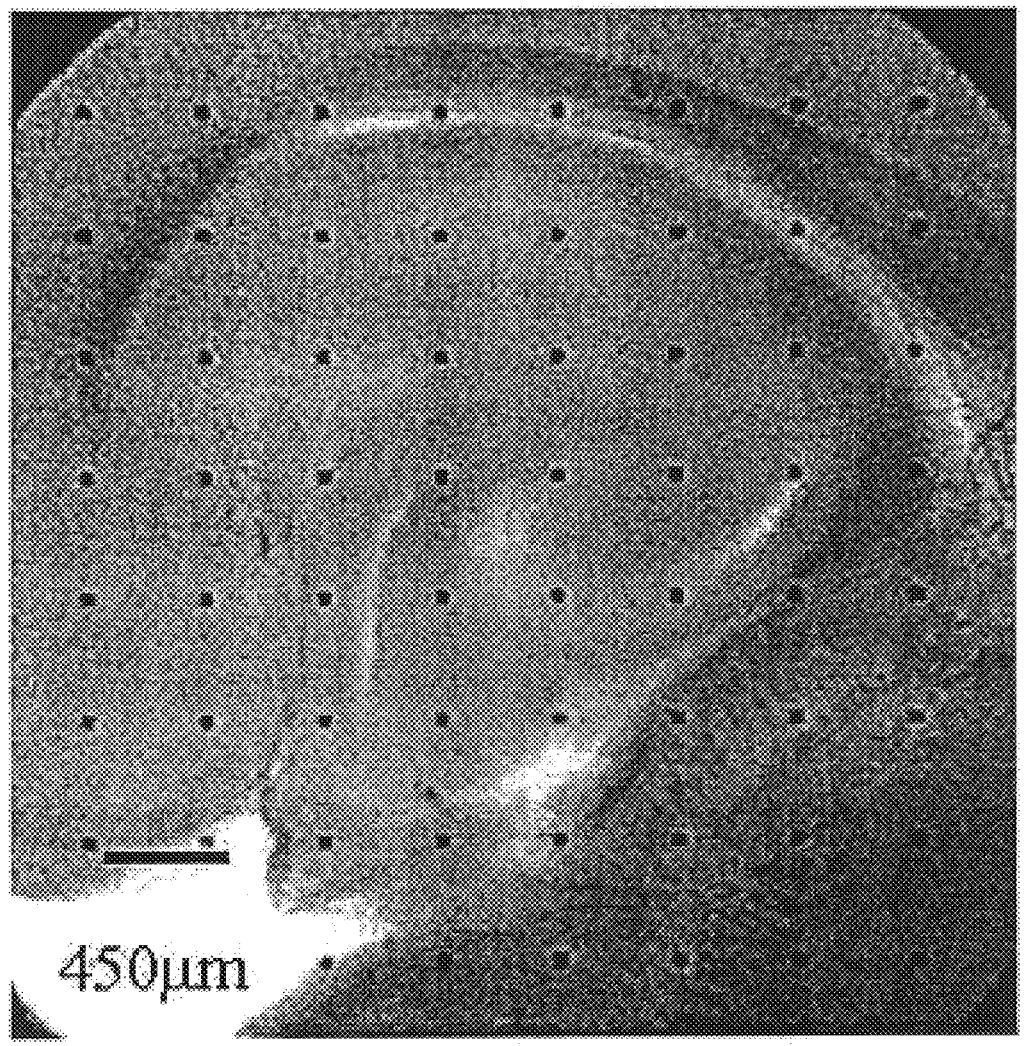

FIG. 14A is a photomicrograph of a hippocampal slice placed atop the MED array. Similarly, FIG. 15A is a photomicrograph of the hippocampal slice atop the MED array used there. The inter-electrode distance was 450 μm. The results of the Fast Fourier Transform on both sets of data are shown (with the significant anatomical boundaries in the background in light gray respectively in FIGS. 14B and 15B). The so-analyzed data indicate that the increased amplitude of the benzodiazepine-infused data is not accompanied by a significant change in the frequency of the waves. As is seen in FIGS. 14C and 15C, both benzodiazepines caused a nearly threefold increase in the power within the 20 Hz band. The increase in power at peak frequency was about 300%.

Ampakine Identification and Characterization

Figure 16A:
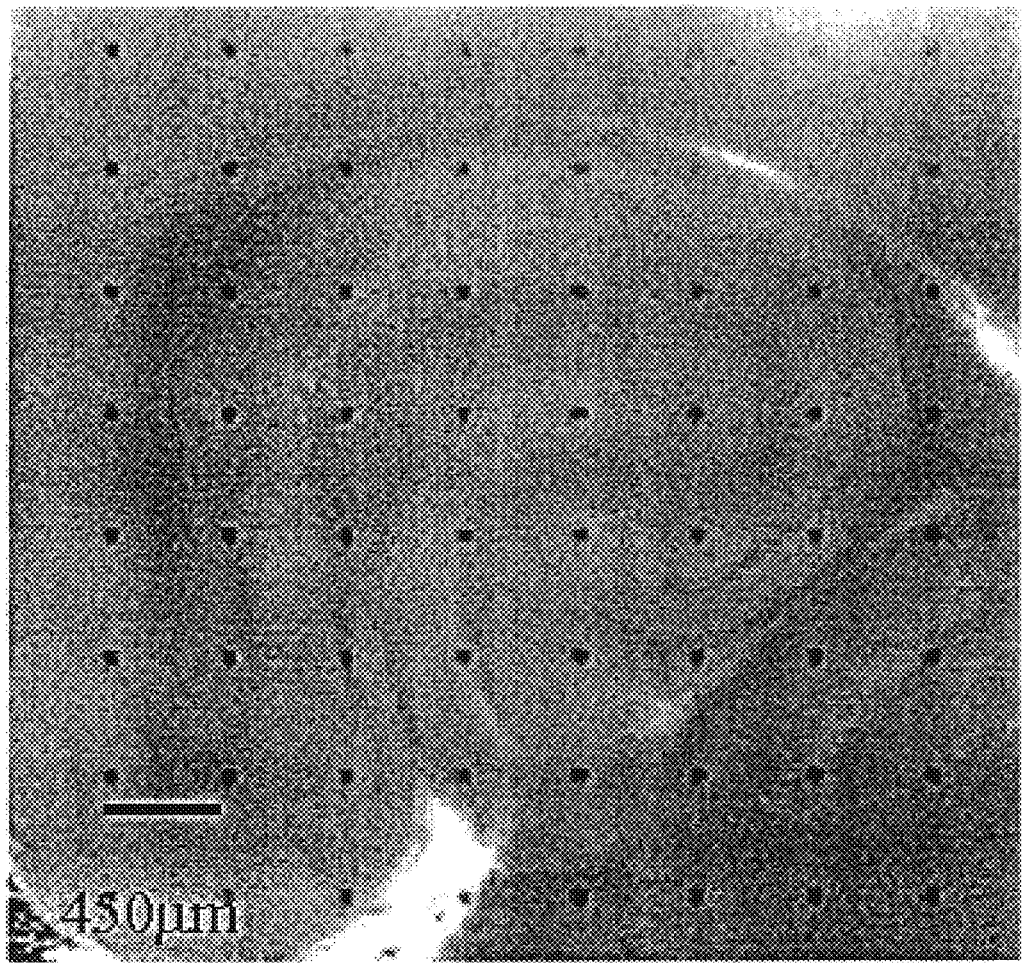
Figure 17A:
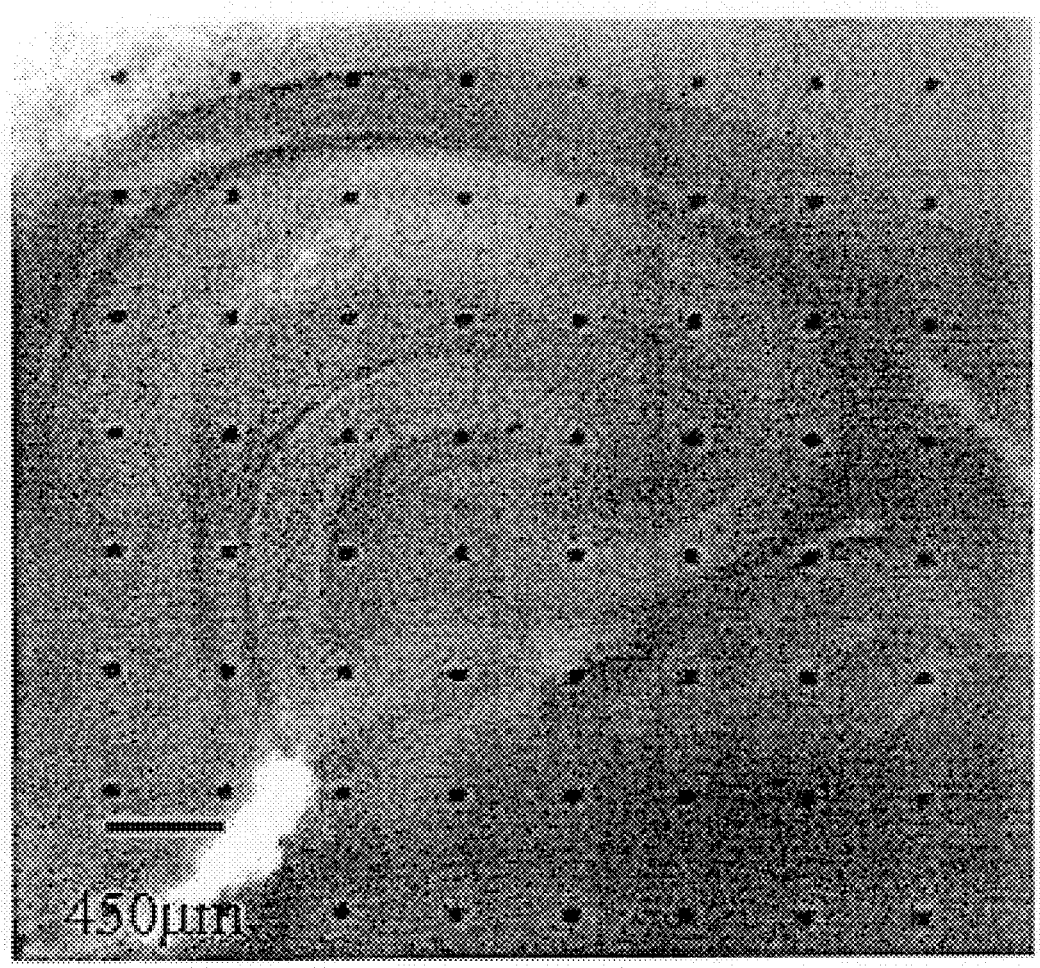
FIGS. 17A–C show the effect of ampakine (CX691) on carbachol-induced beta waves.
Figure 17C:
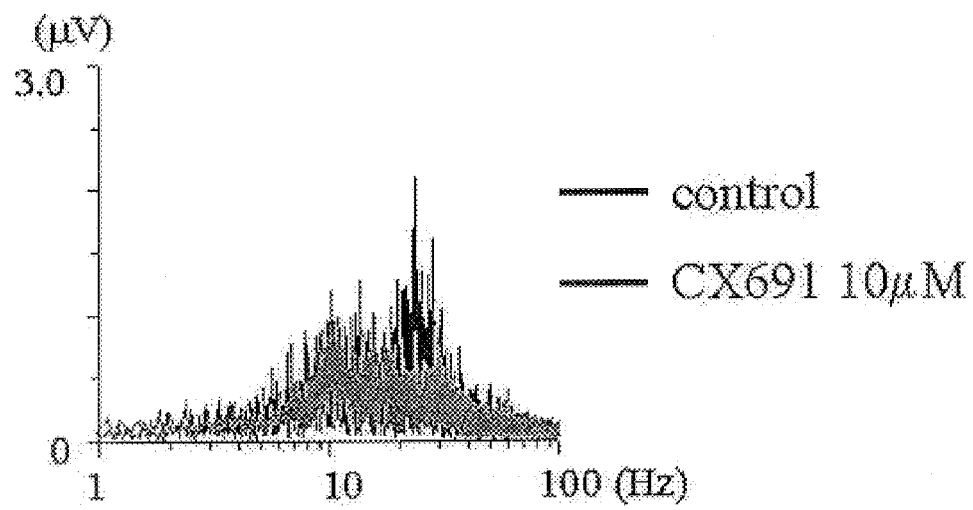
Figure 17B:
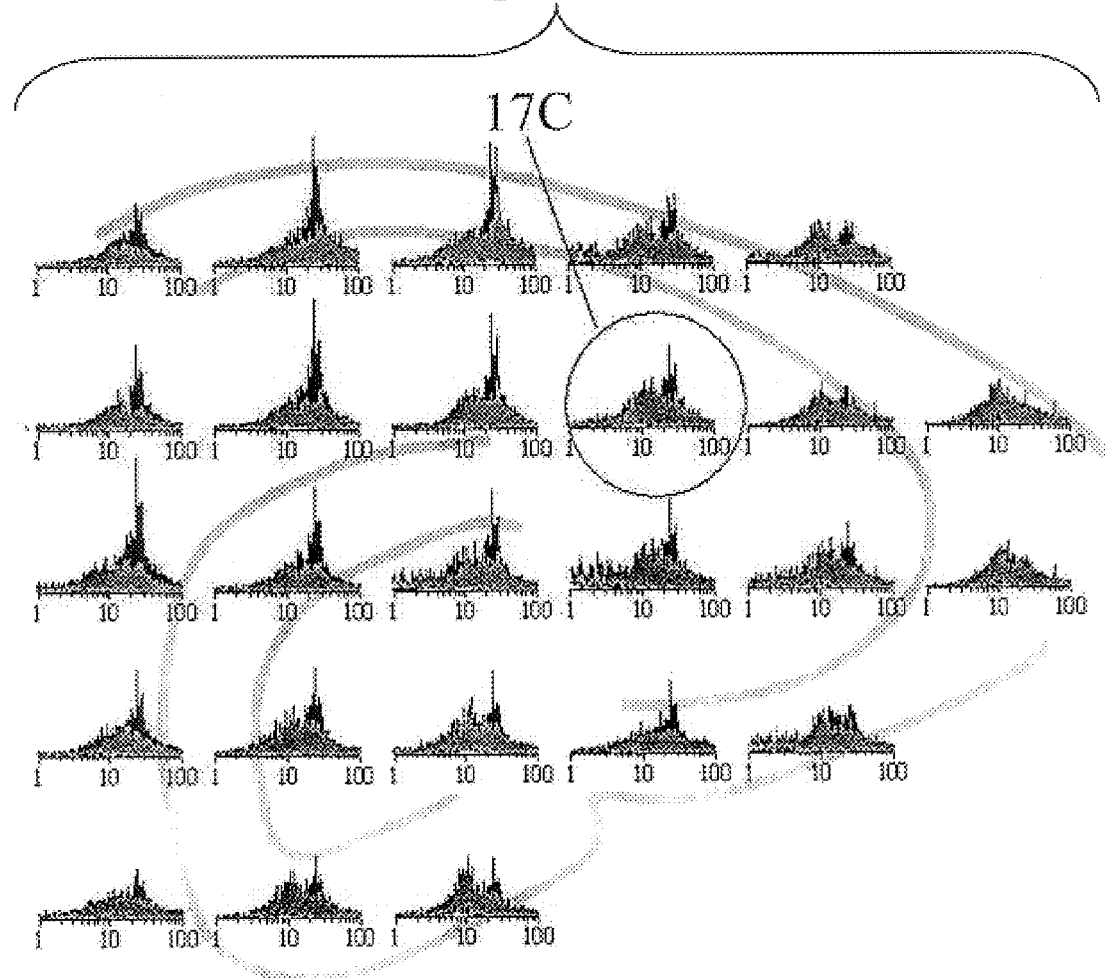

In this Example, a wide spaced MED was used with a hippocampus sample (shown with the underlying microelectrodes respectively in FIGS. 16A and 17A). The potential was again measured for the sample with carbachol alone and subsequently with 10 μM Ampakine (CX614 in FIGS. 16A–C and CX691 in FIGS. 17A–C). The results of the Fast Fourier Transform on both sets of data are shown respectively in FIGS. 16B and 17B (with the significant anatomical boundaries in the background in light gray and thence correlated to the data). The resulting data show the increased frequency of the Ampakine-infused data was also accompanied by a significant change in the amplitude of the waves. Specifically, FIGS. 16C and 17C summarize the frequency spectrum for the specifically chosen recording loci. This shows that the Ampakines not only caused a significant increase in the power within the 20 Hz band (arrow) but also resulted in a 10 Hz shift in the peak.

Ampakines caused a marked reduction in synchrony and a secondary peak of slightly greater than 10 Hz. The resulting data show the decreased amplitude of the Ampakine-infused data is accompanied by a slightly lower shift in the frequency of the waves. Both of the structurally dissimilar Ampakines not only caused a significant decrease in the power within the 20 Hz band but also resulted in a 10

Hz shift in the peak. As shown, the secondary peak appeared to be centered in the dentate gyrus and field CA3 as opposed to the CA1 -subicular localization for pre-Ampakine beta rhythm.

GABA antagonist Identification and Characterization

Antagonists of GABAergic receptors caused a marked reduction, and desynchronized activity punctuated with complex spikes. FIGS. 18A–C and 19A–C respectively show the-effect of bicuculline and picrotoxin on carbachol-induced beta waves.

Figure 18A:
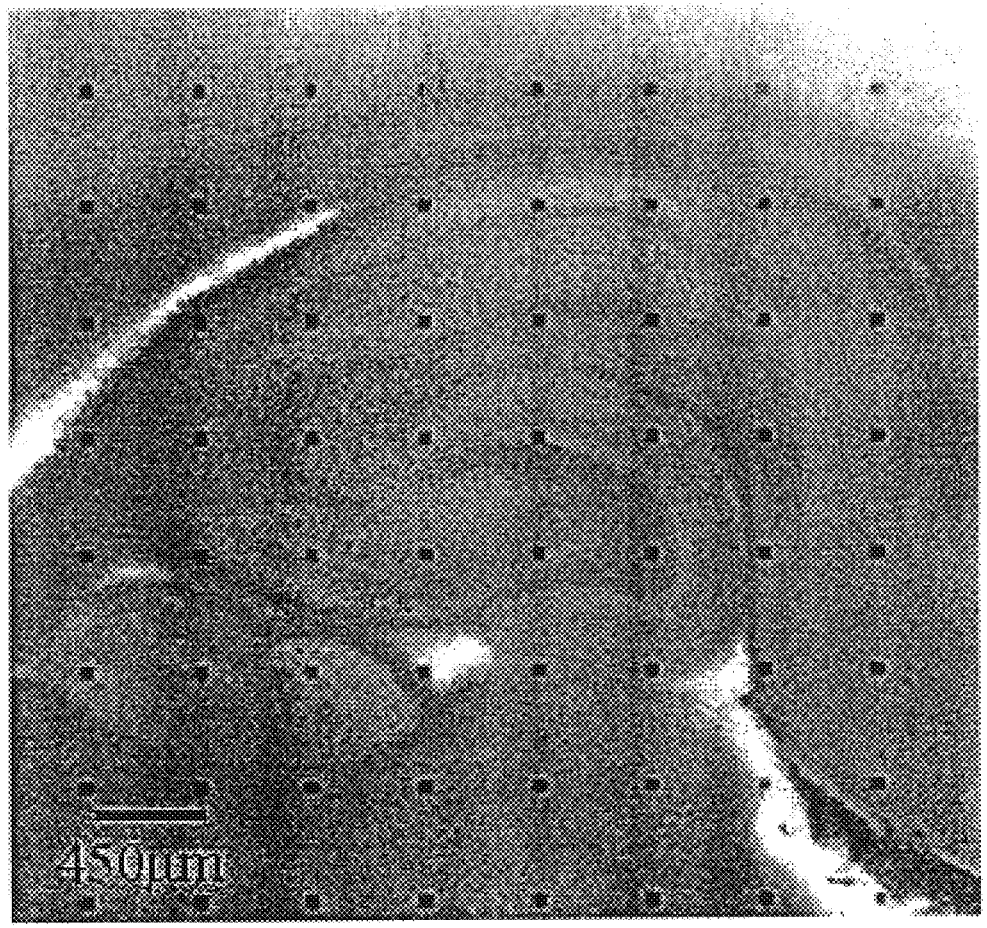
FIGS. 18A–C show the effect of bicuculline on carbachol-induced beta waves.
Figure 18C:
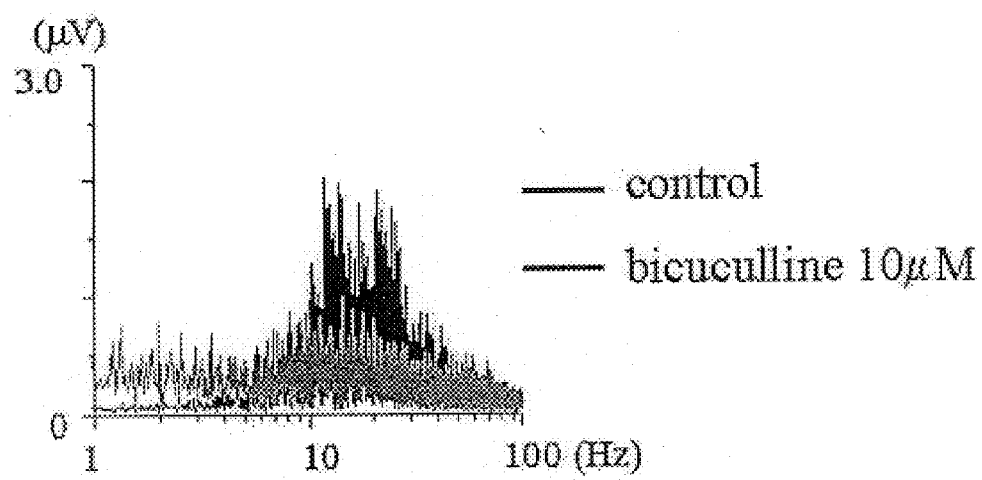

FIG. 18A is a photomicrograph of a hippocampal slice placed atop the MED array. Similarly, FIG. 19A is a photomicrograph of the hippocampal slice atop the MED array used there. The inter-electrode distance was 450 µm. The potentials were measured for the sample with carbachol alone and subsequently with the two listed type GABAergic antagonists: 10 µM bicuculline (FIGS. 18A–C) and 50 µM picrotoxin (FIGS. 19A–C).

Figure 18B:
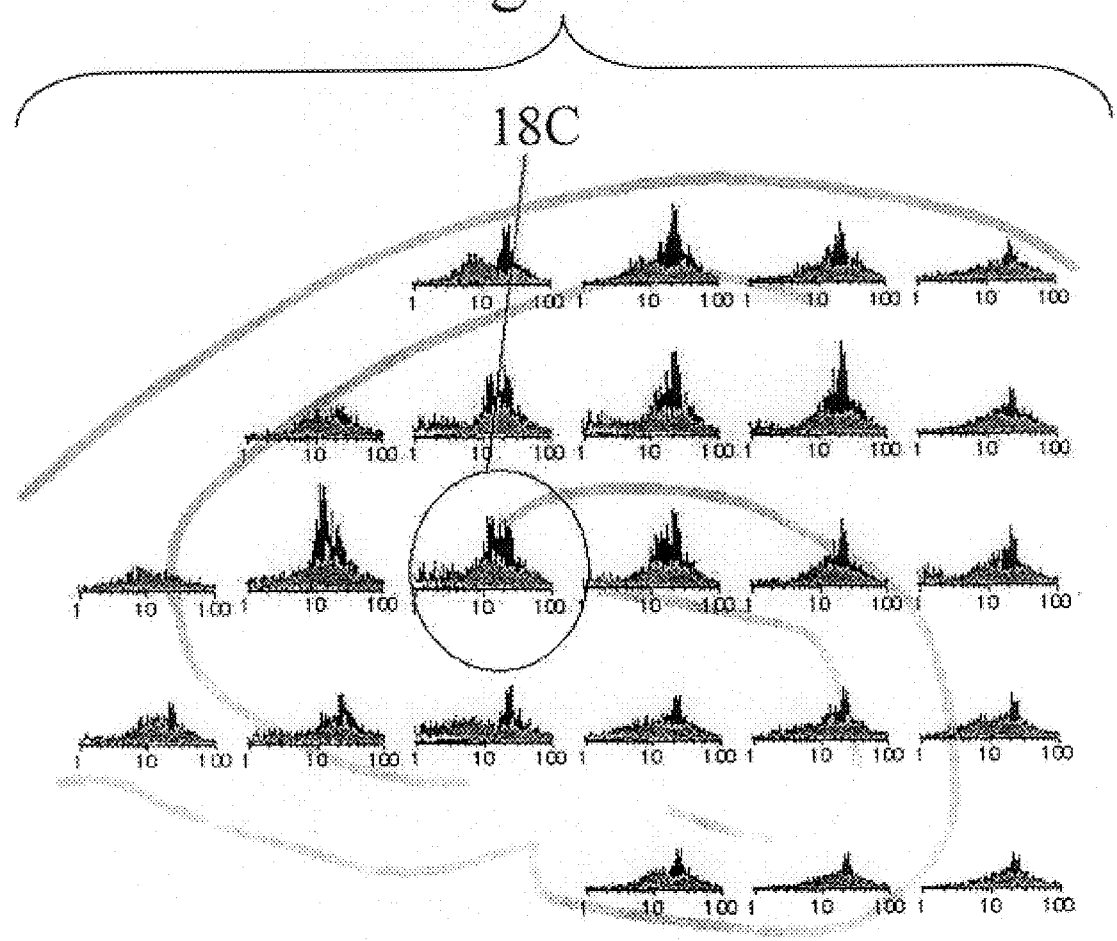
Figure 19A:
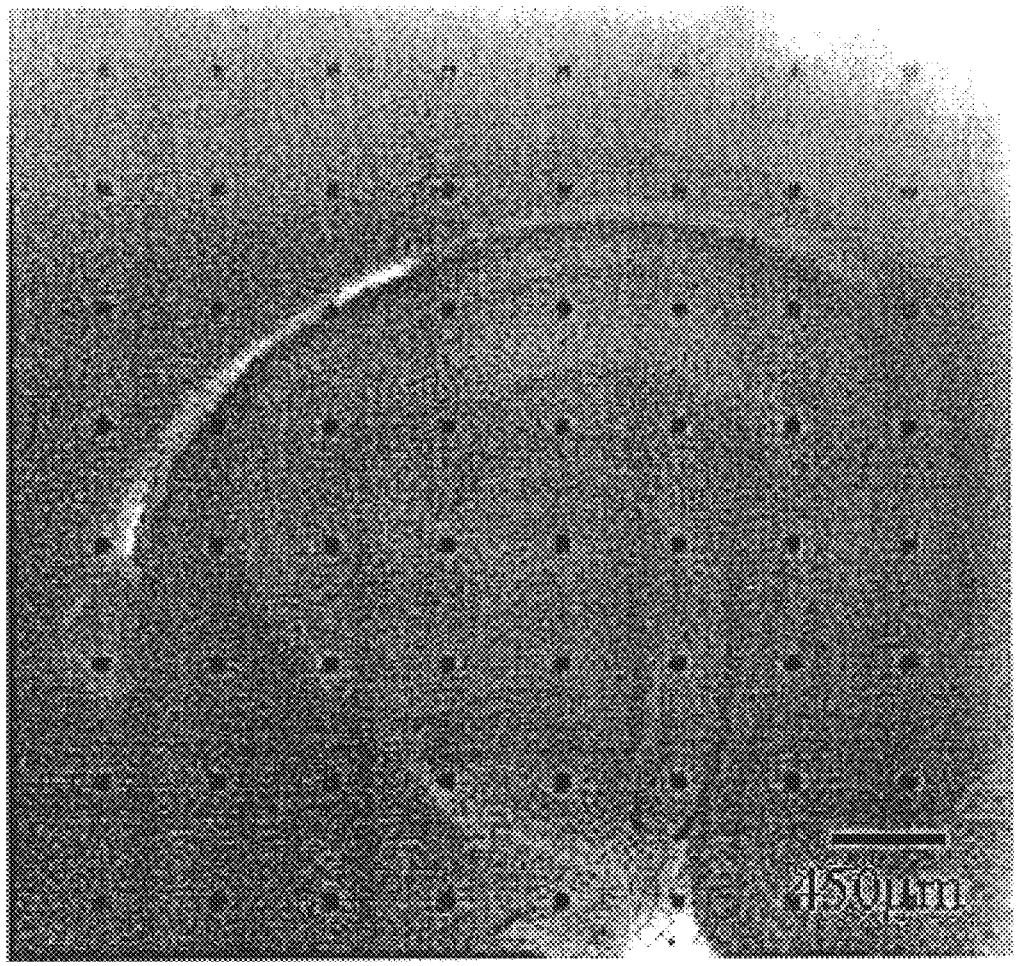

The results of the Fast Fourier Transform on both sets of data are shown respectively in FIGS. 18B and 19B (with the significant anatomical boundaries in the background in light gray and thence correlated to the data). The resulting data showed that the amplitude of the antagonist-infused data markedly decreased after administration of either of the GABAergic antagonists. Said antagonists not only caused a significant decrease in the power within the 20 Hz band but also resulted in a slow component, which consisted of complex spikes. These spikes appeared to be centered in the CA1, subiculum and cortex. FIGS. 18C and 19C show the selected data from FIGS. 18B and 19B.

AMPA Antagonist Identification and Characterization

Figure 20A:
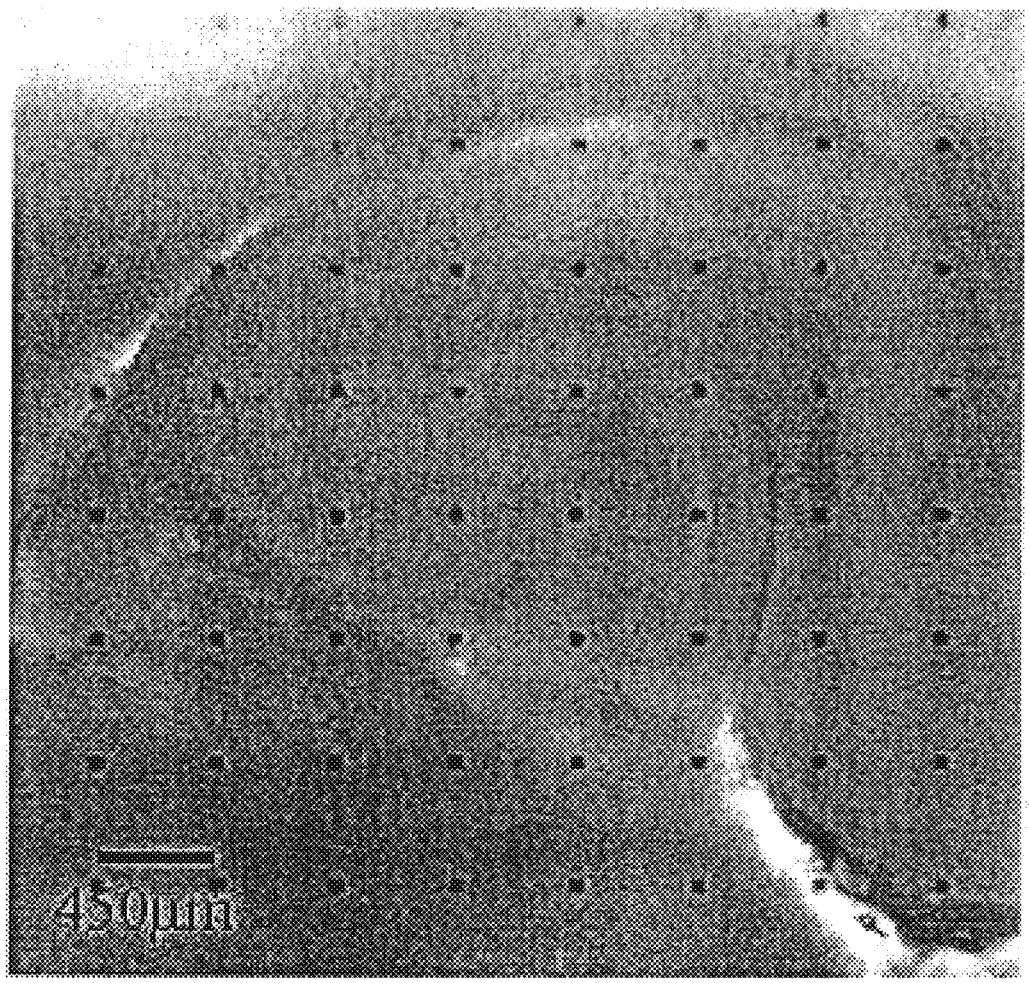
Figure 21A:
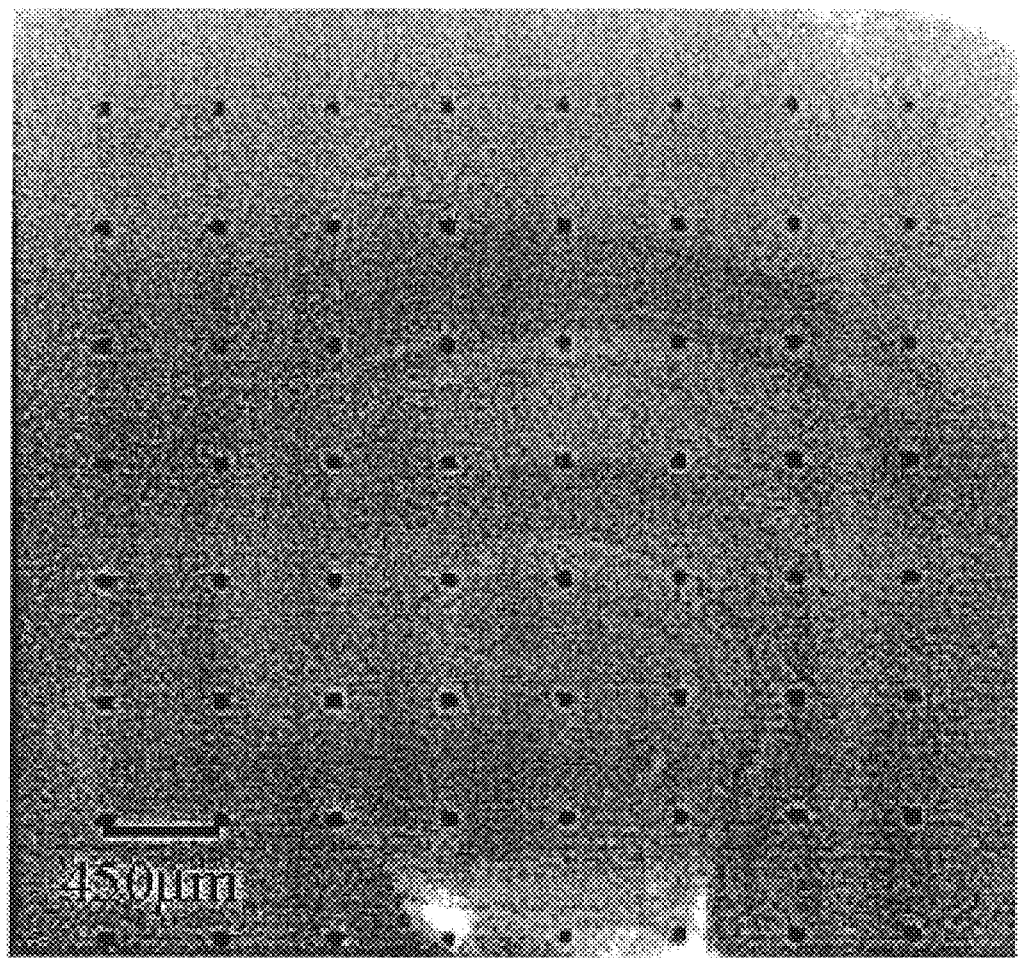
FIGS. 21A–C show the effect of DNQX on carbachol-induced beta waves.
Figure 21C:
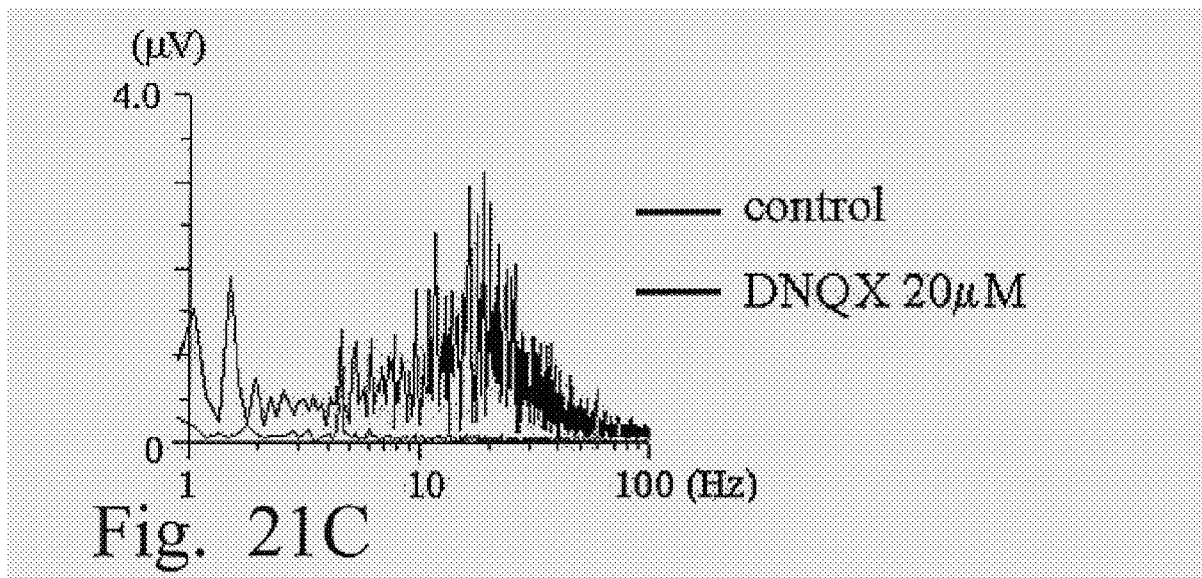
Figure 21B:
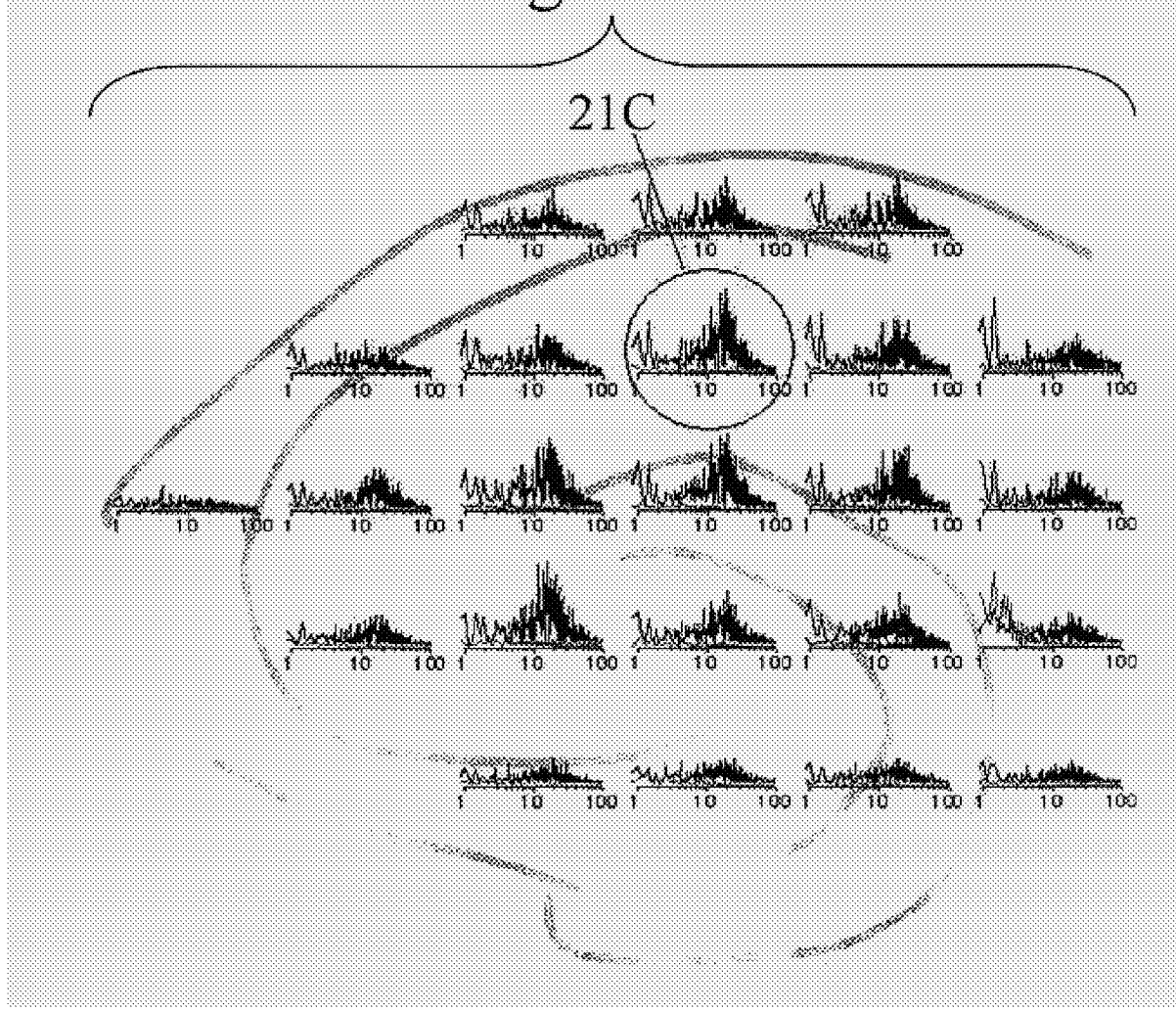
Figure 22A:
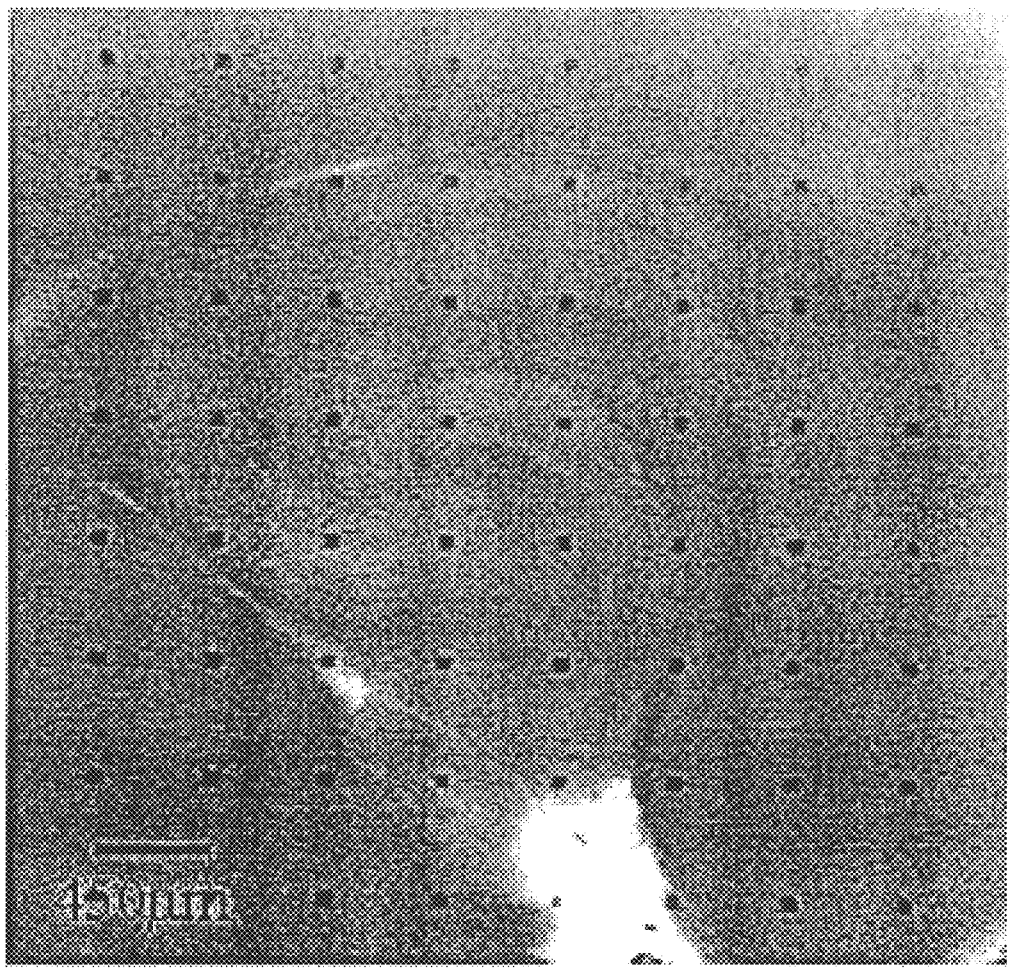
FIGS. 22A–C show the effect of NBQX on carbachol-induced beta waves.
Figure 22C:
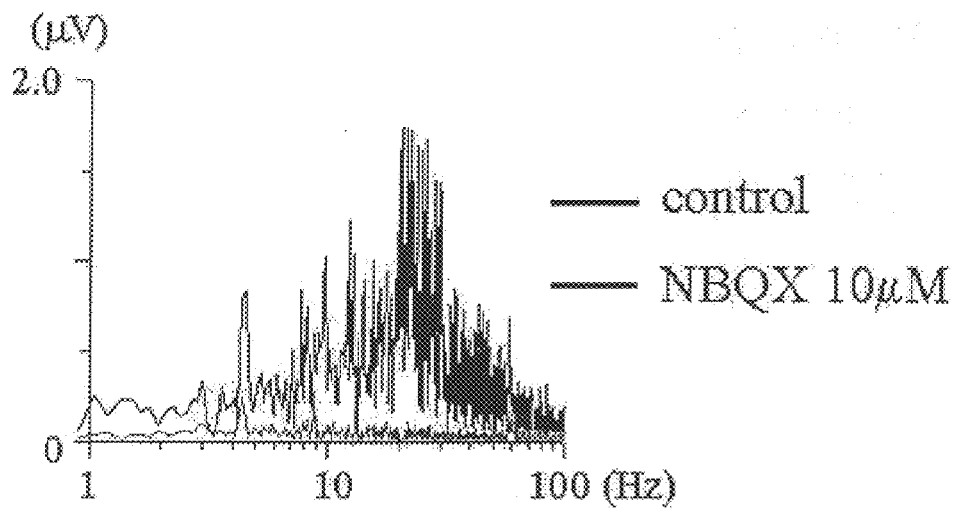
Figure 22B:
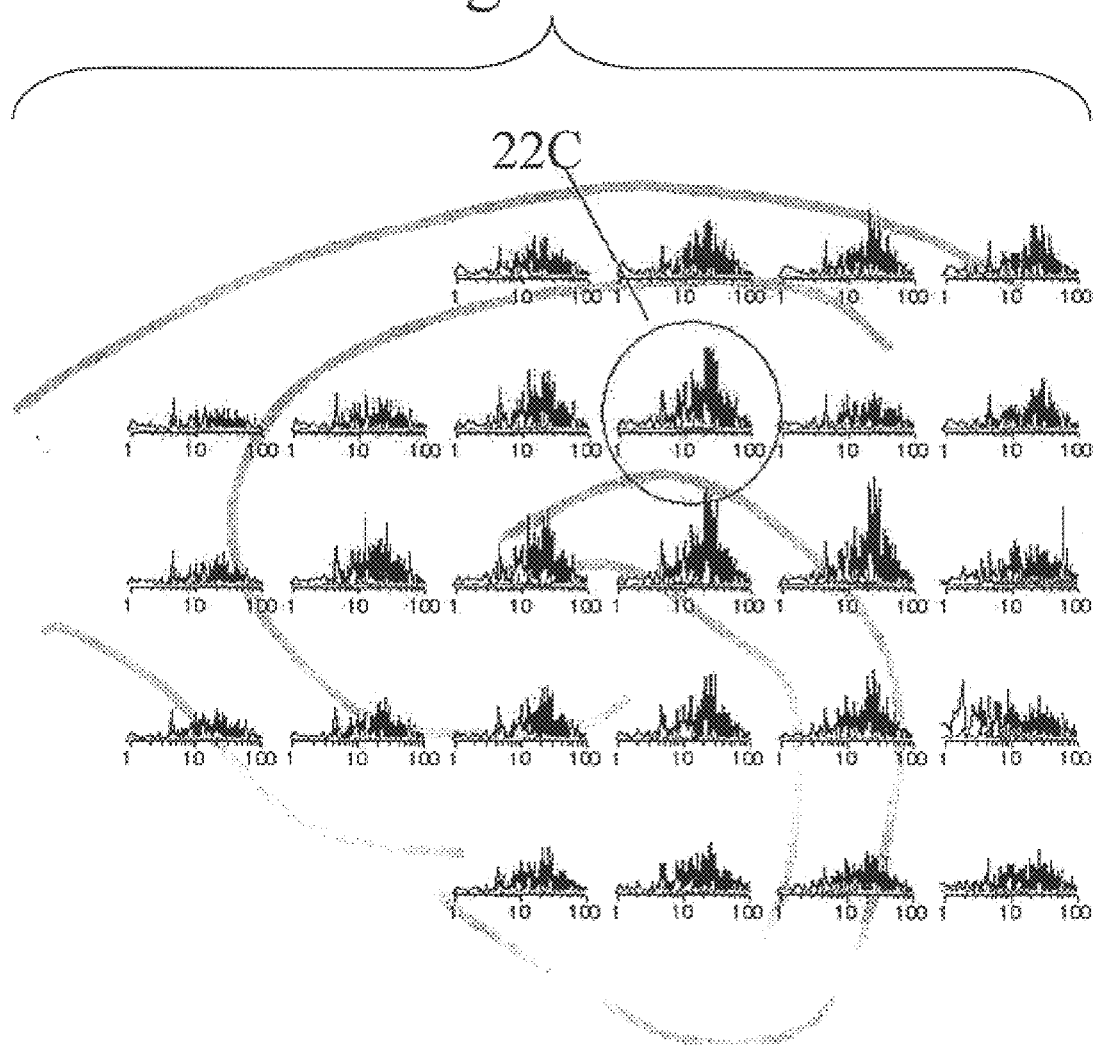

Structurally different antagonists of AMPA–type glutamate receptors caused a very rapid loss of synchronized activity in the previously treated carbachol in vitro neuronal sample. The potentials were measured for the sample with carbachol alone and subsequently with three types glutamate antagonists, one example is 20 µM CNQX (FIGS. 20A–C), one is 20 µM DNQX (FIGS. 21 A–C) and the other is 10 µM NBQX (FIGS. 22A–C). The results of the Fast Fourier Transform on each respective set of data are shown in FIGS. 20B, 21B, and 22B (with the significant anatomical boundaries in the background in light gray and thence correlated to the data). The resulting data show the amplitude data of the antagonist-infused samples was significantly diminished and/or eliminated. All three antagonists caused a significant decrease in the power. FIGS. 20C, 21C, and 22C show the selected data from FIGS. 20B, 21B, and 22B.

SUMMARY

Figure 23:
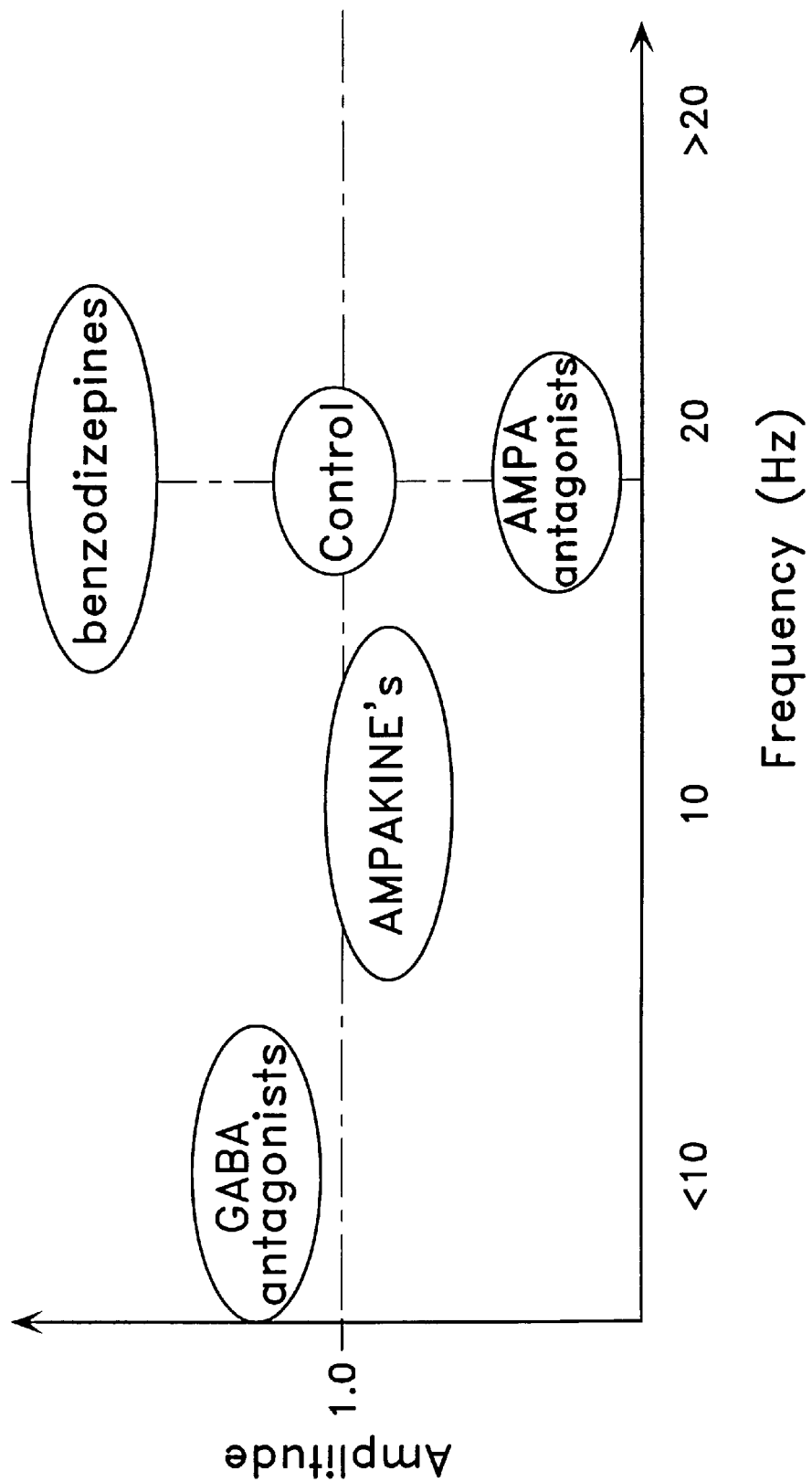
FIG. 23 broadly depicts the predictive results of comparing the oscillatory rhythms before and after the addition of certain classes of psychoactives to neural tissue according to the process of the invention.

FIG. 23 depicts, in a qualitative fashion, the relative differences in evoked potentials caused by the addition of various psychoactives to neural tissue. Observation of or quantification of these relative differences allows detection of and characterization of the various functional groupings and specific members of those groups, e.g., 1. GABA antagonists, such as Bicuculline, □-Hydrastine, Picrotoxin, SR-95531 (Gabazine)
2. AMPA antagonists such as CNQX, DNQX, GYKI 52466 HCl, Joro spider toxin, 1-Naphthyl-acetyl spermine, NS257, NBQX
3. Benzodiazepines (generally, any of a group of chemically similar psychotropic drugs with potent hypnotic and sedative action; used predominantly as antianxiety and sleep-inducing drugs) such as alprazolam, clorazepate, temazepam, flurazepam, Cholrdiazepoxide, Diazepam, Oxazepam, Medazepam, Lorazepam, Flutoprazepam, Fludiazepam, Alprazolam, Oxazolam, Clotiazepam, Etizolam, Flurazepam Hloxazolam, Estazolam, Nitrazepam, Nimetazepam, Flunitrazepam, Trizolam, Rimazafone, flumazenil, bromazepam, etc.
4. AMPA receptor modulators such as Ampakines (Benzoylpiperidine drugs (BDP)): CX516 (BDP-12), CX554 (BDP-20), CX614, CX691, piracetam-like nootropics—Aniracetam, nefiracetam etc.
5. Antipsychotic drugs, generally such as Phenothiazine derivatives, Thioxanthene derivatives, Butyrophenone derivatives (dopamine receptor antagonists), Iminodibenzyl derivatives, Dibenzotthiazepine derivatives, Benzamide derivatives, Theipine derivatives, Benzoisoxazole derivatives (serotonin and dopamine antagonists) and specifically such as: carbamazepine, chlorpromazine, chlorprothixene, clozapine, divalproex sodium, fluphenazine, haloperidol, lithium carbonate, lithium carbonate, lithium citrate, loxapine, mesoridazine, molindone, olanzapine, perphenazine, pimozide, quetiapine, risperidone, thioridazine, thiothixene, trifluoperazine, and triflupromazine
6. Antidepressant drugs, generically such as tricyclic and tetracyclic antidepressants, selective serotonin reuptake inhibitors (SSIRs), serotonin and norepinephrine uptake inhibitors, and monoamine oxidize inhibitors and specifically such as aminoketone, amitriptyline, amoxapine, bupropion, doxepin, desipramine, clomipramine, fluoxetine, fluvoxamine, Hypericum, Hypericum perforatum, imipramine, isocarboxazid, maprotiline, mirtazapine, nefazodone, nortriptyline, nortriptyline, paroxetine, phenylpiperazine, phenelzine, protriptyline, sertraline, tranylcypromine, trazodone, triazolopyridine, trimipramine, and venlafaxine
7. Central nervous system stimulants, generically such as xanthines and amphetamines and specifically such as dextroarnphetamine, Ephedra, Ephedra sinica, Metamphetamine, Methylphenidate, methylphenidate, and pemoline
8. Anticonvulsants generically such as barbiturates, oxazolidinediones derivatives, carbonic anhydrase inhibitors, benzodiazepines, and GABA transaminase inhibitors; specifically such as carbamazepine, clobazam, dezinamide, divalproex sodium, felbamate, flunarizine, fosphenytoin, gabapentin, lamotrigine, levetiracetam, midazolam, milacemide, MK-801, oxcarbazepine, phenobarbital, primidone, progabide, stiripentol, tiagabine, topiramate, valproic acid, vigabatrin, and zonisamide.
9. Antianxiety drugs, generically such as antihistamines, barbiturates, benzodiazepines, beta-blockers, buspirone, propanediols, selective serotonin reuptake inhibitors (SSIR's), serotonin receptor agonists, and tricyclic antidepressants; specifically such as alprazolam, buspirone, chlordiazepoxide, clomiprarnine, clorazepate, diazepam, fluoxetine, fluvoxamine, halazepam, lorazepam, meprobamate, oxazepam, phenobarbital, Piper, Piper methysticum, prazepam, and propranolol.
10. Hypnotics (generally, hyptonics are drugs that are pertinent to sleep or hypnosis or are agents that cause an insensitivity to pain by inhibiting afferent impulses or by inhibiting the reception of sensory impressions in the cortical centers of the brain, thus causing partial or complete unconsciousness) Hypnotics generally include sedatives, analgesics, anesthetics, and intoxicants, and are sometimes called sornifacients and soporifics when used to induce sleep. Specific hypnotics include aliphatic alcohols, barbiturates, benzodiazepines, Hypericum, Hypericum perforatum, melatonin, certain non-barbiturates, Piper, Piper methysticum, Valeriana, and Valeriana officinalis 11. Narcotic analgesics such as opioid receptor agonists and specifically such as heroin and morphine.

12. Dopaminergic agents such as arnantadine, benztropine, carbidopa/levodopa, and trihexyphenidyl.

REFERENCES

Behrends J C, Bruggencate G (1993) Cholinergic modulation of synaptic inhibition in the guinea pig hippocampus in vitro: excitation of GABAergic intemeurons and inhibition of GABA–release. J Neurophysiol 69:626–629

Benson D M, Blitzer R D, Landau E M (1988) An analysis of the depolarization produced in guinea pig hippocampus by cholinergic receptor stimulation. J Physiol (London) 404:479–496

Boddeke HWGM, Best R, Boeijinga P H (1997) Synchronous 20 Hz rhythmic activity in hippocampal networks induced by activation of metabotropic glutamate receptors in vitro. Neuroscience 76:653–658.

Buzsaki G. (1986). Hippocampal sharp waves: origin and significance. Brain Res 398: 242–252.

Charpak S, Parae D, Llinas R (1995). The entorhinal cortex entrains fast CA1 monosynaptic component of the perforant path. Eur J Neurosci 7: 1548–1557.

Chrobak J J, Buzsaki G (1998). Gamma oscillations in the entorhinal cortex of the freely behaving rat. J Neurosci, 18: 388–398.

Dickson C T, Alonso A (1997) Muscarinic induction of synchronous population activity in the entorhinal cortex J Neurosci 17:6729–6744.

Fisahn A, Pike F G, Buhl E H, Paulsen O (1998) Cholinergic induction of network oscillations at 40 Hz in the hippocampus in vitro. Nature 394:186–189

Freeman W J (1975) Mass action in the nervous system. New York: Academic Press.

Frotscher M, LeranthC (1985) Cholinergic innervation of the rat hippocampus as revealed by choline acetyltransferase immunocytochemistry: a combined light and electron microscopic study. J Comp Neurol 239:237–246

Funahashi M, Stewart M (1998) Properties of gamma-frequency oscillations initiated by propagating population bursts in retrohippocampal region of rat brain slices. J Physiol (Lond) 510:191–208

Gray C M, Singer W (1989) Stimulus-specific neuronal oscillation columns of cat visual cortex. Proc Natl Acad Sci USA 56:1698–1702

Haberly L, Shepherd G (1973). Current density analysis of summed evoked potentials in opossum prepyriform cortex. J Neurophysiol, 36: 789–803.

Hajos N, Papp ECS, Acsady L, Levy A, Freund T F (1998) Distinct intemeuron types express M2 muscarinic receptor immunoreactivity on their dendrites or axon terminals in the hippocampus. Neuroscience 82:355–376

Howland B, Lettvin J, McCulloch W, Pitts W, Wall P (1955). Reflex inhibition by dorsal root interaction. J Neurophysiol, 18: 1–17.

Horowitz J M, Freeman W J, Stoll P J (1973) A neural network with a background level of excitation in the cat hippocampus. Int J Neurosci 5:113–123

Kay L M, Freeman W J (1998) Bidirectional processing in the olfactory-limbic axis during olfactory behavior. Behav Neurosci 112:514–553

Ketchum K L, Haberly L B (1993) Membrane currents evoked by afferent fiber stimulation in rat piriform cortex. I. Current source density analysis. J. Neurophysiol 69: 248–260.

Kolta A, Ambros-Ingerson J, Lynch G (1996) Early and late components of AMPA-receptor mediated field potentials in hippocampal slices. Brain Res. 737: 133–145.

Konopacki J, MacIver M B, Bland B H, Roth S H (1987) Carbachol-induced EEG 'theta' activity in hippocampal brain slice. Brain Res 405:196–198.

Landfield P W, McGaugh J L, Tusa R J (1972) Theta rhythm: a temporal correlate of memory storage processes in the rat. Science 175:87–89.

Larson J, Wong D, Lynch G. (1986). Patterned stimulation at the theta frequency is optimal for the induction of hippocampal long-term potentiation. Brain Res., 368: 347–350.

Larson J, Lynch G. (1986). Induction of synaptic potentiation in hippocampus by patterned stimulation involves two events. Science 232: 985–988.

Larson J, Xiao P, Lynch G (1993) Reversal of LTP by theta frequency stimulation. Brain Res 600:97–102.

Leung LS (1982) Nonlinear feedback model of neuronal populations in hippocampal CA1 region. J Neruophysiol 47:845–868.

Leung L S (1985) Spectral analysis of hippocampal EEG in the freely, moving rat: effects of centrally active drugs and relations to evoked potentials. Electroencephalogr Clin Neurophysiol 60:65–77.

Levey A 1, Edmunds S M, Koliatsos V, Wiley R G, Helman C J (1995) Expression of m1–m4 muscarinic acetylcholine receptor proteins in rat hippocampus and regulation by cholinergic innervation. J Neurosci 15:4077–4092.

Lewis P R, Shute CCD (1967) The cholinergic limbic system: projections to hippocampal formation, medial cortex, nuclei of the ascending cholinergic reticular system, and the subfomical organ and supra-optic crest. Brain 90:521–40.

Lynch G, Rose G, GallC (1978) Anatomical and functional aspects of the septohippocampal projections. In: Functions of the septo-hippocampal system (Ciba foundation symposium 58), pp5–24. Amsterdam: Elsevier.

MacVicar B A, Tse F W Y (1989) Local neuronal circuitry underlying cholinergic rhythmical slow activity in CA3 area of rat hippocampus. J Physiol (London) 417:197–212.

Madison D V, Lancaster B, Nicoll R A (1987) Voltage clamp analysis of cholinergic action in the hippocampus. J Neurosci 7:733–741.

Matthews D A, Salvaterra P M, Crawford G D, Houser C R, Vaughn J E (1987) An immunocytochemical study of choline acethltransferase-containing neurons and axon terminals in normal and partially deafferented hippocampal formation. Brain Res 402:30–43.

Mitzdorf U (1985). Current source-density method and application in cat cerebral cortex: Investigation of evoked potentials and EEG phenomena. Physiol Rev, 65: 37–100.

Mosko S, Lynch G, Cotman C W (1973) Distribution of the septal projections to the hippocampus of the rat. J Comp Neurol 152:163–174.

Mott D D, Lewis D V. (1991). Facilitation of the induction of long-term potentiation by GABAB receptors. Science, 252: 1718–1720.

Nakajima Y, Nakajima S, Leonard R J, Yamaguchi K (1986) Acetylcholine raises excitability by inhibiting the fast transient potassium current in cultured hippocampal neurons. Proc Natl Acad Sci USA 83:3022–3026.

Nicholson C (1973). Theoretical analysis of field potentials in anisotropic ensembles of neuronal elements. IEEE Trans Biomed Eng, 20: 278–288.

Nicholson C, Freeman J (1975). Theory of current source-density analysis and determination of conductivity tensor for anuran cerebellum. J Neurophysiol, 38: 356–368.

Nicholson C, Llinas R (1975). Real time current source density analysis using multi-electrode array in cat cerebellum. Brain Res, 100: 418–424.

Oka H, Shimono K, Ogawa R, Sugihara H, Taketani M (1999) A new planar multielectrode array for extracellular recording: application to hippocampal acute slice. J Neurosci Methods 93:61–67.

Pitler T A, Alger B E (1992) Cholinergic excitation of GABAergic interneurons in the rat hippocampal slice. J Physiol (Lond). 450:127–142.

Racine R, Livingston K, Joaquin A(1975) Effects of procaine hydrochloride, diazepam, and diphenylhydantoin on seizure development n cortical and subcortical structures in rats. Electroenceph Clin Neurophysiol 38:355–365.

Sarter M; Bruno J P. (1998). Age-related changes in rodent cortical acetylcholine and cognition: main effects of age versus age as an intervening variable. Brain Res., 27: 143–156.

Singer W (1998) Consciousness and structure of neuronal representations. Philos Trans R Soc LondBBiol Sci 353:1829–1840.

Stumpf C (1965) Drug action on the electrical activity of the hippocampus. Int Rev Neurosci 8:77–138.

Traub R D, Spruston N, Soltesz I, Konnerth A. (1998). Gamma-frequency oscillations: A neuronal population phenomenon, regulated by synaptic and intrinsic cellular processes, and inducing synaptic plasticity. Prog. Neurobiol., 55: 563–575.

Traub R D, Whittington M A, Buhl E H, Jefferys J G R, Faulkner H J. (1999). On the mechanism of the gamma→beta frequency shift in neuronal oscillations induced in rat hippocampal slices by tetanic stimulation. J. Neurosci., 19: 1088–1105.

Traub R D, Whittington M A, Colling S B, Buzsaki G B, Jefferys G R (1995) Analysis of the gamma rhythm in the rat hippocampus in vitro and in vivo. J Physiol (London) 493:471–484.

Vanderwolf C H (1969) Hippocampal electrical activity and voluntary movement in the rat. Electroenceph Clin Neurophysiol 26:407–418.

Vertes R P, Kocsis B (1997) Brainstem-dienchephalo-septhippocampal systems controlling the theta rhythm of the hippocampus. Neuroscience 81:893–926.

Williams J H, Kauer J A (1997) Properties of carbachol-induced oscillatory activity in rat hippocampus. J Neurophysiol 78:2631–2640.

We claim as our invention:

1. A process for the detection of psychoactive compounds in an in vitro neuronal tissue sample comprising:
    a) comparing oscillations of extracellular potentials in said in vitro neuronal tissue sample which tissue sample has been contacted with a psychoactive compound candidate sample composition with a baseline to assess differences between said oscillations and said baseline, and
    b) detecting the presence or absence of a psychoactive compound in said candidate sample composition based upon the differences between said oscillations and said baseline.

2. The process of claim 1 further comprising the step of contacting said psychoactive compound candidate sample composition with said in vitro neuronal tissue sample.

3. The process of claim 2 further comprising the step of detecting a baseline of oscillations of extracellular potential in said in vitro neuronal tissue sample prior to contacting said psychoactive compound candidate sample composition with said in vitro neuronal tissue sample.

4. The process of claim 1 further comprising the step of characterizing the composition of said psychoactive compound based upon differences between said baseline and said oscillations of extracellular potential.

5. The process of claim 4 wherein said differences are values selected from the group of differences between frequency, amplitude, and combinations of said frequency of and said amplitude of extracellular potentials and said baseline.

6. The process of claim 1 further comprising a rendering step of subjecting said resulting oscillations of extracellular potential and said baseline to a Fast Fourier Transform.

7. The process of claim 1 further comprising a rendering step of performing a current source density analysis upon a temporal sequence of said oscillations and said baseline to produce current flow patterns.

8. The process of claim 1 wherein said comparing step comprises the step of comparing the amplitude or frequency of said oscillations with said baseline to detect the presence or absence of a psychoactive compound in said candidate sample composition.

9. The process of claim 1 wherein said comparing step comprises the step of comparing a multitude of said oscillations with a corresponding multitude of said baselines to detect the presence or absence of a psychoactive compound in said candidate sample composition.

10. A device for the detection and characterization of psychoactive compounds in an in vitro neuronal tissue sample comprising:
    a) a cell potential measuring electrode array having plural microelectrodes connectable to a computer, said microelectrodes adapted both to detect synchronous oscillations of extracellular potential in said in vitro neuronal tissue sample and to provide electrical stimulation to said in vitro neuronal tissue sample,
    b) a sample introducer for placing a psychoactive compound candidate sample composition into contact with said in vitro neuronal tissue sample, and
    c) said computer, said computer including programming for i.) detecting oscillations of extracellular potential in said in vitro neuronal tissue sample both before and after introducing said psychoactive compound candidate sample composition to said in vitro neuronal tissue sample, and ii.) comparing said before and after oscillations of extracellular potential to detect the presence or absence of a psychoactive compound and, if detected, to characterize said psychoactive compound based upon differences between said before and after oscillations of extracellular potential.

11. The device of claim 10 wherein said baseline and said oscillations of extracellular potential are spatial arrays of values selected from the group of frequency of extracellular potentials, amplitude of extracellular potentials, and combinations of said frequency of and said amplitude of extracellular potentials and wherein said computer includes comparator programming for comparing said before and after spatial array of values.

12. The device of claim 11 wherein said computer includes programming for subjecting said before and after spatial array of values to Fast Fourier Transform.

13. The device of claim 12 wherein said computer comprises a Digital Signal Processor.

14. The device of claim 10 wherein said computer includes programming for performing a current source density analysis upon a temporal sequence of extracellular potentials to produce current flow patterns.

15. The device of claim 10 wherein said computer includes programming for comparing the amplitude or frequency of said before and after values to detect the presence or absence of a psychoactive compound in said candidate sample composition.

16. A method for the detection and characterization of psychoactive compounds in an in vitro neuronal tissue sample comprising the steps of:
   a) detecting a baseline value of oscillations of extracellular potential in said in vitro neuronal tissue sample,
   b) contacting a candidate sample composition with said in vitro neuronal tissue sample,
   c) detecting a resulting value of said oscillations of extracellular potential in said in vitro neuronal tissue sample, and
   d) comparing said resulting value of oscillations with said baseline value to detect the presence or absence of a psychoactive compound in said candidate sample composition.

17. The method of claim 16 further comprising the step of rendering said resulting oscillations of extracellular potential value and said baseline value of oscillations of extracellular potential respectively to produce a calculated resulting value and a calculated baseline value and
   wherein said comparing step comprises comparing said calculated resulting value with said calculated baseline value to detect the presence or absence of a psychoactive compound in said candidate sample composition.

18. The method of claim 17 further comprising the step of characterizing a detected psychoactive compound based upon the differences in said calculated resulting value and said calculated baseline value.

19. The method of claim 16 further comprising the step of adding a stimulating composition prior to detection of said baseline value of oscillations of extracellular potential.

20. The method of claim 19 wherein said stimulating composition comprises one or more compounds which facilitate or mimic the actions of acetylcholine, serotonin, or catecholamines.

21. The method of claim 19 wherein said stimulating composition comprises one or more cholinomimetic compounds.

22. The method of claim 19 wherein said stimulating composition comprises carbachol.

23. The method of claim 19 wherein said stimulating composition comprises a co-culture tissue sample.

24. The method of claim 16 further comprising the step of saving said baseline value of oscillations of extracellular potential.

25. The method of claim 16 wherein said baseline value of oscillations of extracellular potential and said resulting oscillations of extracellular potential value are selected from the group consisting of theta, beta, and gamma EEG waves.

26. The method of claim 25 wherein said baseline value of EEG wave and said resulting EEG wave value are beta waves.

27. The method of claim 16 wherein said baseline value of oscillations of extracellular potential and said resulting oscillations of extracellular potential value are spatial arrays of values selected from the group of frequency of extracellular potentials, amplitude of extracellular potentials, and combinations of said frequency of and said amplitude of extracellular potentials.

28. The method of claim 16 wherein said rendering step comprises the step of performing a Fast Fourier Transform upon each of said resulting oscillations of extracellular potential value and said baseline value of oscillations of extracellular potential respectively to produce said calculated resulting value and said calculated baseline value.

29. The method of claim 28 wherein said rendering step comprises subjecting said resulting oscillations of extracellular potential value and said baseline value of oscillations of extracellular potential to a Fast Fourier Transform in a Digital Signal Processor.

30. The method of claim 28 wherein said rendering step comprises subjecting said resulting oscillations of extracellular potential value and said baseline value of oscillations of extracellular potential to a Fast Fourier Transform in a general purpose computer.

31. The method of claim 16 wherein said rendering step comprises the step of performing a current source density analysis upon a temporal sequence of said calculated resulting values and said calculated baseline values to produce current flow patterns.

32. The method of claim 31 wherein said rendering step comprises subjecting said resulting oscillations of extracellular potential value and said baseline value of oscillations of extracellular potential to a Fast Fourier Transform in a Digital Signal Processor.

33. The method of claim 31 wherein said rendering step comprises subjecting said resulting oscillations of extracellular potential value and said baseline value of oscillations of extracellular potential to a Fast Fourier Transform in a general purpose computer.

34. The method of claim 28 wherein said comparing step comprises the step of comparing the amplitude or frequency of said calculated resulting value with said calculated baseline value to detect the presence or absence of a psychoactive compound in said candidate sample composition.

35. The method of claim 28 wherein said comparing step comprises the step of comparing a multitude of said calculated resulting value with a corresponding multitude of said calculated baseline value to detect a variation of oscillations of extracellular potential in said in vitro neuronal tissue sample and detect the presence or absence of a psychoactive compound in said candidate sample composition.

36. The method of claim 16 further comprising the step of inducing baseline oscillations of extracellular potential by electrically stimulating said in vitro neuronal tissue sample prior to detection of said baseline value of oscillations of extracellular potential.

37. The method of claim 16.wherein said resulting oscillations of extracellular potential value and said baseline value of oscillations of extracellular potential are spatial distributions of values selected from the group of frequency of extracellular potentials, amplitude of extracellular potentials, and combinations of said frequency of and said amplitude of extracellular potentials.

38. The method of claim 37 wherein spatial distribution of potentials are obtained by comparing arrays of potentials with an anatomical feature of in vitro neuronal tissue sample.

39. The method of claim 38 wherein said anatomical feature is observed by microscope.

40. The method of claim 38 wherein said anatomical feature is analyzed by microscopic image and image processing algorithms.

41. The method of claim 16 wherein said rendering step further comprises the step of calculating regional distribution of said calculated baseline value and said calculated resulting value.

42. The method of claim 28 wherein said rendering step further comprises the step of calculating regional distribution of said calculated baseline value and said calculated resulting value.

43. The method of claim 33 wherein said rendering step further comprises the step of calculating regional distribution of said calculated baseline value and said calculated resulting value.

44. The method of claim 41 wherein regional distribution of calculated baseline value and calculated resulting value are obtained by comparing the calculated values with an anatomical feature of in vitro neuronal tissue sample.

45. The method of claim 42 wherein regional distribution of calculated baseline value and calculated resulting value are obtained by comparing the calculated values with an anatomical feature of in vitro neuronal tissue sample.

46. The method of claim 42 wherein regional distribution of calculated baseline value and calculated resulting value are obtained by comparing the calculated values with an anatomical feature of in vitro neuronal tissue sample.

47. The method of claim 44 wherein said anatomical feature is observed by microscope.

48. The method of claim 45 wherein said anatomical feature is observed by microscope.

49. The method of claim 41 wherein said anatomical feature is observed by microscope.

50. The method of claim 44 wherein said anatomical feature is analyzed by microscopic image and image processing algorithms.

51. The method of claim 45 wherein said anatomical feature is analyzed by microscopic image and image processing algorithms.

52. The method of claim 40 wherein said anatomical feature is analyzed by microscopic image and image processing algorithms.

* * * * *

UNITED STATES PATENT AND TRADEMARK OFFICE
CERTIFICATE OF CORRECTION

PATENT NO. : 6,511,817 B1
DATED : January 28, 2003
INVENTOR(S) : Gary Lynch et al.

Page 1 of 1

It is certified that error appears in the above-identified patent and that said Letters Patent is hereby corrected as shown below:

<u>Title page,</u>
Item [73], Assignee, please replace "University of California" with
-- The Regents of the University of California --.

Signed and Sealed this

Fourth Day of January, 2005

JON W. DUDAS
*Director of the United States Patent and Trademark Office*